United States Patent
Uesugi et al.

(10) Patent No.: US 8,231,523 B2
(45) Date of Patent: Jul. 31, 2012

(54) ENDOSCOPIC SYSTEM EQUIPPED WITH GAS SUPPLY APPARATUS

(75) Inventors: Takefumi Uesugi, Tokyo (JP); Daisuke Sano, Tokyo (JP); Yoshimine Kobayashi, Tokyo (JP); Mutsumi Ohshima, Tokyo (JP); Takehiro Nishiie, Toyko (JP); Atsuhiko Kasahi, Yokohama (JP); Kenji Noda, Toyko (JP)

(73) Assignee: Olympus Corporation (JP)

( * ) Notice: Subject to any disclaimer, the term of this patent is extended or adjusted under 35 U.S.C. 154(b) by 1970 days.

(21) Appl. No.: 11/194,966

(22) Filed: Aug. 2, 2005

(65) Prior Publication Data

US 2006/0030751 A1 Feb. 9, 2006

(30) Foreign Application Priority Data

Aug. 4, 2004 (JP) ................................ 2004-228441

(51) Int. Cl.
*A61B 1/04* (2006.01)
*A61B 1/12* (2006.01)
*A61M 37/00* (2006.01)

(52) U.S. Cl. .......... 600/118; 600/158; 600/159; 604/23; 604/26

(58) Field of Classification Search .................. 600/104, 600/118, 156, 158, 159, 120; 604/23–26
See application file for complete search history.

(56) References Cited

U.S. PATENT DOCUMENTS

| | | | | |
|---|---|---|---|---|
| 4,464,169 A | * | 8/1984 | Semm | 604/26 |
| 4,509,507 A | * | 4/1985 | Yabe | 600/158 |
| 4,715,372 A | * | 12/1987 | Philippbar et al. | 606/2 |
| 4,844,052 A | * | 7/1989 | Iwakoshi et al. | 600/157 |
| 5,006,109 A | * | 4/1991 | Douglas et al. | 604/26 |
| 5,022,382 A | * | 6/1991 | Ohshoji et al. | 600/156 |
| 5,098,375 A | * | 3/1992 | Baier | 604/23 |
| 5,139,478 A | * | 8/1992 | Koninckx et al. | 604/26 |
| 5,246,419 A | * | 9/1993 | Absten | 604/26 |
| 5,328,458 A | * | 7/1994 | Sekino et al. | 604/23 |
| 5,423,741 A | * | 6/1995 | Frank | 604/26 |
| 5,439,441 A | * | 8/1995 | Grimsley et al. | 604/26 |
| 5,740,801 A | * | 4/1998 | Branson | 600/407 |
| 5,800,381 A | * | 9/1998 | Ognier | 604/26 |
| 5,897,525 A | * | 4/1999 | Dey et al. | 604/67 |
| 6,299,592 B1 | | 10/2001 | Zander | 604/26 |
| 6,402,714 B1 | * | 6/2002 | Kraft-Kivikoski | 604/23 |
| 6,632,194 B1 | * | 10/2003 | Mehner et al. | 604/26 |
| 7,476,213 B2 | * | 1/2009 | Uesugi et al. | 604/26 |
| 2005/0171401 A1 | * | 8/2005 | Woltjen | 600/118 |

FOREIGN PATENT DOCUMENTS

JP 2000-139827 5/2000

* cited by examiner

*Primary Examiner* — Matthew J Kasztejna
*Assistant Examiner* — Ryan Henderson
(74) *Attorney, Agent, or Firm* — Ostrolenk Faber LLP

(57) ABSTRACT

An endoscopic system includes an endoscope having a delivery member available to supply a body cavity of a specimen and, in addition thereto, a gas supply apparatus from which predetermined gas is supplied to a body cavity via a delivery member. The endoscopic system further includes a determination unit that determines whether or not there is a status in which, the gas supply device needs to supply gas to the body cavity, and a control unit that selectively and automatically control a permit and stop for the gas supply to be implemented by the gas supply apparatus depending on a determined result of the determination unit, which are formed in a unitary structure with, for instance, the gas supply unit.

10 Claims, 27 Drawing Sheets

ENDOSCOPIC SYSTEM EQUIPPED WITH GAS SUPPLY APPARATUS

CROSS REFERENCE TO RELATED APPLICATIONS

The present application relates to and incorporates by reference to Japanese Patent Application No. 2004-228441 filed on Aug. 4, 2004, the entire content of which is hereby incorporated by reference.

BACKGROUND OF THE INVENTION

1. Technical Field of the Invention

The present invention relates to an endoscopic system equipped with, in addition to an endoscope and a light source device, a gas supply apparatus for supplying gas to a body cavity (such as abdominal cavity and luminal cavity) of an object to be examined via a gas supply channel of the endoscope for achieving observation.

2. Related Art

Attempts have heretofore been undertaken to carry out laparoscopic surgeries (hereinafter also referred to as surgical operations) without opening an abdominal cavity with a view to implementing treatment on a patient with minimally invasive capability. During such surgical operations, a first trocar, through which, for instance, an endoscope for observation is guided to the abdominal cavity, and a second trocar, through which a treatment tool is guided to a treatment site, are inserted to an inside of the abdominal cavity of a patient. Additionally, with a view to ensuring a visual field of the endoscope and ensuring an expanded area through which the treatment tool is manipulated, an abdominal insufflation gas is introduced to the abdominal cavity by an abdominal insufflation device through the trocar, mentioned above, or another trocar. Such an abdominal insufflation device is known from, for instance, Japanese Patent Provisional Publication No. 2000-139827.

Injecting an abdominal insufflation gas into the abdominal cavity results in a status wherein the abdominal cavity is distended. Therefore, it becomes possible to execute necessary treatment or the like by using the endoscope, inserted to the abdominal cavity via the first trocar, and observing a treatment site while confirming that the treatment tool has been inserted through the second trocar.

Also, as for abdominal insufflation gas, for instance, use is made of a carbon dioxide gas ($CO_2$, which is referred to as a carbon dioxide gas), which is easy to be absorbed by a living body.

In recent years, as new attempts, in addition to a technology of using the endoscope inserted to the luminal cavity, such as larger intestine, through the above-described first trocar, therapeutic procedures have been conducted for treating a treatment site upon inserting a flexiblescope into the luminal cavity. With such therapeutic procedures, the treatment site can be specified with the endoscope inserted in the abdominal cavity and another endoscope inserted in the luminal cavity for curative treatment.

In implementing such procedures, since there are needs for carbon dioxide gas to be separately supplied to both the abdominal cavity and the luminal cavity, the use of an abdominal insufflation device of the related art merely in a single unit is insufficient. This results in a need for preparing a system, i.e., a so-called laparoscopic surgery operation system, which is based on the abdominal insufflation device of the related art. The laparoscopic surgery operation system includes an integrated system that is comprised of a first light source device and a cameral control unit to which a rigid-scope, available to be inserted to an abdominal cavity via a trocar, is connected; a second light source device and a second cameral control unit to which a flexiblescope, having an inserter section available to be inserted to a luminal cavity, is connected; the related art abdominal insufflation device and a first carbon dioxide gas container from which carbon dioxide gas is supplied to the abdominal cavity via the trocar; an endoscopic carbon dioxide gas regulator (Endoscopic $CO_2$ Regulator: hereinafter abbreviated as ECR) and a second carbon dioxide gas container from which carbon dioxide gas is supplied, as observation gas, to the luminal cavity via the inserter section and a manipulator of the flexiblescope and a gas supply and water supply conduit formed in a universal cord; and a controller electrically connected to the respective component parts for executing operation controls.

That is, the second light source device is continuously supplied with, in place of air delivered from a gas supply and water supply pump, carbon dioxide gas, which has been originally used in the flexiblescope, from the ECR. This carbon dioxide gas is supplied into the luminal cavity via the manipulator of the flexiblescope and the gas supply and water supply conduit.

However, such a system allows carbon dioxide gas to be supplied to the luminal cavity only when an operator executes a closing operation of a bore portion formed in a gas supply and water supply button of the flexiblescope. Stated another way, under circumstances where the operator does not close the gas supply and water supply button, carbon dioxide gas is continuously released from the bore portion to the atmosphere during a period in which the ECR supplies carbon dioxide gas to the delivery member. That is, this results in continuous consumption of carbon dioxide gas from the second carbon dioxide gas container even under a non-observing condition wherein no observation for the luminal cavity is implemented, causing a waste of gas.

Further, the laparoscopic surgery operation system, mentioned above, takes the form of a structure in which in addition to the light source device, the camera control unit and the abdominal insufflation device that are used in normal operations, the ECR are separately added. For this reason, there is a possibility wherein the operator forgets to turn off a power switch of the ECR after the operation has been completed. Such a case also results in consumption of carbon dioxide gas in a continuous and useless fashion.

SUMMARY OF THE INVENTION

The present invention has been completed with the above issues in mind and has an object to provide an endoscopic system that can suppress wasteful consumption of carbon dioxide gas serving as observation gas.

According to one aspect of the present invention, there is provided an endoscopic system comprising an endoscope having a delivery member available to supply gas to a body cavity of a specimen, a gas supply apparatus supplying predetermined gas to the body cavity via the delivery member, a determination device determining whether or not there is a status in which the gas supply apparatus needs to supply the predetermined gas to the body cavity and a control unit selectively and automatically controlling a permit and a stop for the gas to be supplied by the gas supply apparatus depending on a determined result of the determination device.

According to another aspect of the present invention, there is provided an endoscopic system comprising an endoscope having a delivery member available to supply gas to a body cavity of a specimen, a container storing therein the gas, a gas supply apparatus supplying the gas, contained in the container, to the body cavity under a pressure appropriate thereto, a light source device relaying the gas, delivered from the gas supply apparatus, to a delivery member of the endoscope and having at least a lamp that supplies an image picking-up illumination light to the endoscope, a determination device determining whether or not there is a status in which the gas supply apparatus needs to supply the gas to the body cavity, and a control unit selectively and automatically controlling a permit and a stop for the gas to be supplied by the gas supply apparatus depending on a determined result of the determination device.

According to still another aspect of the invention, there is provided an endoscopic system comprising a first endoscope through which an observation is available for an abdominal cavity of a specimen, a second endoscope through which an observation is available for a luminal cavity of the specimen, a container storing therein the gas, a gas supply apparatus supplying the gas, contained in the container, to the abdominal cavity and the luminal cavity upon regulating the gas to pressure values different from each other and appropriate for the abdominal cavity and the luminal cavity, respectively, a light source device relaying the gas, delivered from the gas supply apparatus, for the luminal cavity to a delivery member of the endoscope and having at least a lamp that supplies an imaging illumination light to the endoscope, a delivery member supplying the gas, delivered from the gas supply apparatus, for the abdominal cavity to the abdominal cavity, a determination device determining whether or not there is a status in which the gas supply apparatus needs to supply the gas, and a control unit selectively and automatically controlling a permit and a stop for the gas to be supplied by the gas supply apparatus depending on a determined result of the determination device.

According to a further aspect of the invention, there is provided a method of supplying gas, delivered from a gas supply apparatus, to a body cavity of a specimen via a delivery member of an endoscope. With such a method, determination is made whether or not there is a status in which the gas supply apparatus needs to supply the gas to the body cavity and, depending on the determined result, a permit and a stop for the gas to be supplied by the gas supply apparatus are selectively and automatically controlled.

With such a structure, under a gas supply state wherein observation gas is supplied to the delivery member of the endoscope, the gas supply state can be switched to the gas supply state of the gas supply interruptive state. Therefore, observation gas, stored in the gas container, can be prevented from being wastefully consumed.

DETAILED DESCRIPTION OF THE PREFERRED EMBODIMENTS

A variety of preferred embodiments according to the present invention will now be described with reference to the accompanying drawings.

First Embodiment

Referring to FIGS. 1 to 5, an endoscopic system, equipped with a gas supply apparatus, of a first embodiment according to the present invention is described below.

Figure 1:
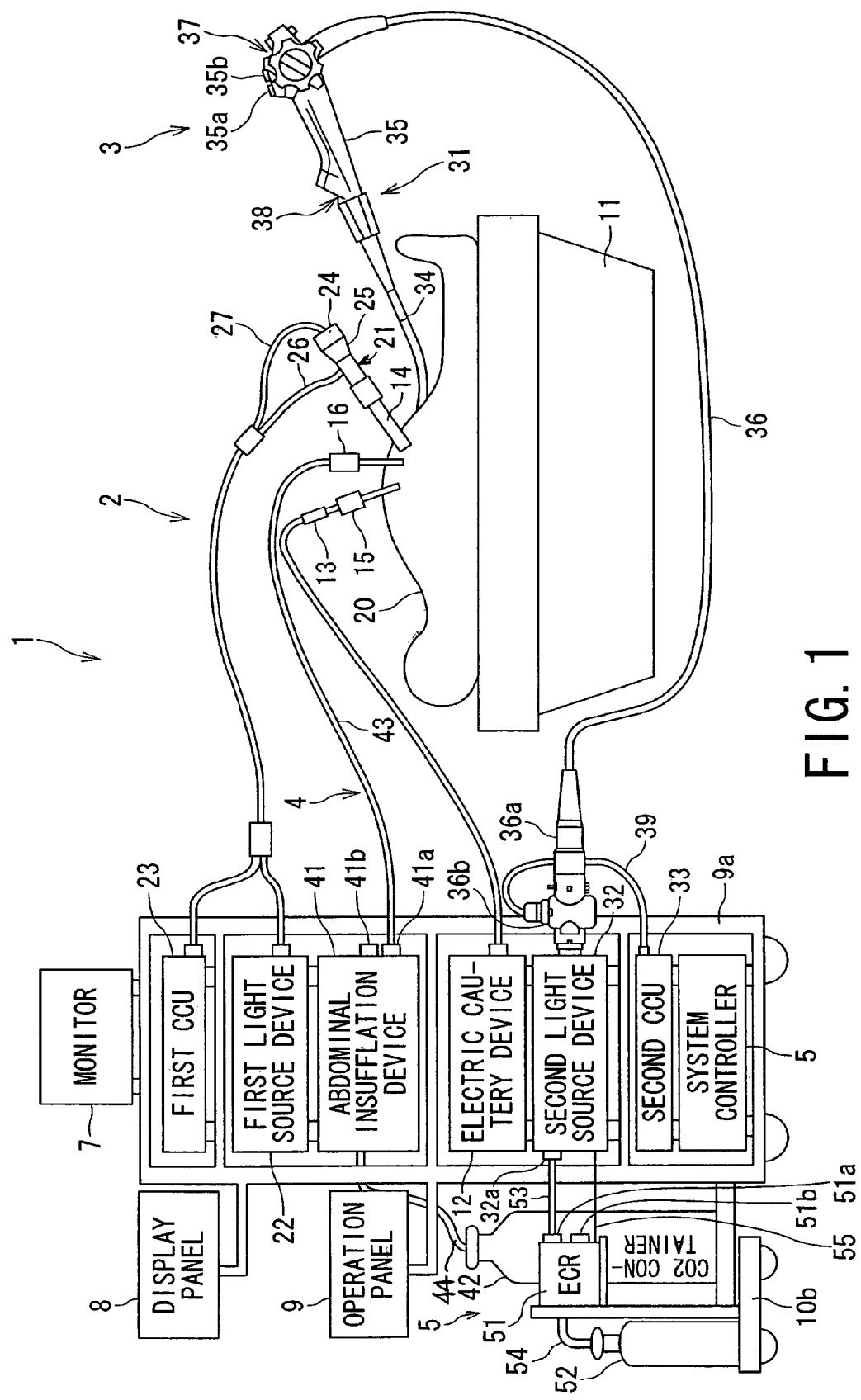
FIG. 1 is an overall structural view of an endoscopic system, equipped with a gas supply apparatus, of a first embodiment according to the present invention.

As shown in FIG. 1, with the presently filed embodiment, the endoscopic system of the present invention is implemented as a laparoscopic surgery operation system (hereinafter referred to as a surgery operation system) 1. The surgery operation system 1 is mainly comprised of component parts, such as a first endoscopic system 2, a second endoscopic system 3, a first gas supply apparatus 4, a second gas supply apparatus 5, a system controller 6, a monitor 7 serving as a display device, a centralized display panel 8, a centralized operation panel 9 and carts 10a, 10b.

Also, as shown in FIG. 1, reference numeral 11 designates an operation bed on which a patient 20 lies down. Reference numeral 12 designates an electric cautery device. Connected to the electric cautery device 12 is an electric cautery 13 that serves as an operation tool. Reference numerals 14, 15, 16 designate trocars, respectively, that are available to be inserted to a stomach portion of the patient. A first trocar 14 serves as a trocar through which an endoscope, described below, of the first endoscope system 2 is guided to an abdominal cavity AC. A second trocar 15 serves as a trocar through which a treatment tool, such as the electric cautery 13, for executing the excision or treatment of a tissue, is guided to the abdominal cavity. A third trocar 16 serves as a trocar through which an abdominal cavity insufflation gas is supplied from an abdominal insufflation device (described bellow), which forms the gas supply apparatus 4, is guide to the abdominal cavity.

The first endoscope system 2 is comprised of main component parts, such as a rigidscope 21 serving as a first endoscope with, for instance, a hard inserter section, a first light source device 22, a first camera control unit (hereinafter abbreviated as a first CCU (Camera Control Unit)) 23 and an endoscopic camera 24.

The inserter section (not shown) of the rigidscope 21 is inserted to and placed in the first trocar 14. Provided in the inserter section is an observation optical system, composed of relay lenses (not shown) through which an optical image of a subject is transmitted, and an illumination optical system, composed of a light guide (not shown). Provided on a base portion of the inserter section is an eyepiece 25 through which the optical image, transmitted from the observation optical system, can be observed. Detachably mounted to the eyepiece 25 is the endoscopic camera 24. Detachably disposed on the eyepiece 25 is the endoscopic camera 24. Disposed inside the endoscopic camera 24 is an image pickup device (not shown).

The first light source device 22 supplies an illumination light to the rigidscope 21. The first CCU 23 serves to perform a drive control of an image pickup element of the endoscopic camera 24 and convert an electric signal, resulting from photoelectric conversion of an image focused on the image pickup element, into an image signal. The image signal, converted by the first CCU 23, is outputted to, for instance, the monitor 7 or the centralized display panel 8. Upon execution of such operations, a display screen of the monitor 6 or centralized display panel 8 provides a display of an endoscopic image of the subject resulting from the rigidscope 21.

Also, the rigidscope 21 and the first light source device 22 are optically connected to each other via a light guide cable 26 that extends from a side face of the base portion of the rigidscope 21. The first CCU 23 and the endoscopic camera 24 are connected to each other via an image pickup cable 27.

The second endoscope system 3 is mainly comprised of a flexiblescope 31 serving as a second endoscope and having a soft inserter section 34 adapted to be inserted to an inside of a luminal cavity, such as a large intestine or the like, a second light source device 32, serving as an illumination light supplier, and a second camera control unit (hereinafter referred to as second CCU) 33.

In the present embodiment and subsequent embodiments to be described later, the body cavities of an object to be examined (such as patient) include an abdominal cavity and a luminal cavity such as a large intestine.

The flexiblescope 31 is comprised of the inserter section 34, set forth above, a manipulator 35 and a universal chord 36. Provided on the manipulator 35 is a gas supply and water supply switch 35a, a suction button 35b, a curving operation knob 37 that allows a curving portion (not shown in the drawing figure) to be curved in operation, and a treatment tool insertion port 38 formed in communication with a treatment tool channel that is not shown. An endoscope connector 36a is provided on the base portion of the universal chord 36. Extending from the endoscope connector 36a is a water supply tube 64 that is connected to a water supply tank 60.

Provided in the second light source device 32 are an illumination lump 63 (see FIG. 2) serving as an illumination unit for supplying an illumination light to the endoscope 31 and a gas supply and water supply pump 59 (see FIG. 2) or the like serving as a gas supply unit for supply gas or water. Detachably connected to the second light source device 32 is an endoscope connector 36a that are equipped with a gas supply fitting 36c (see FIG. 2) and a light source connector 36d (see FIG. 2).

Figure 2:
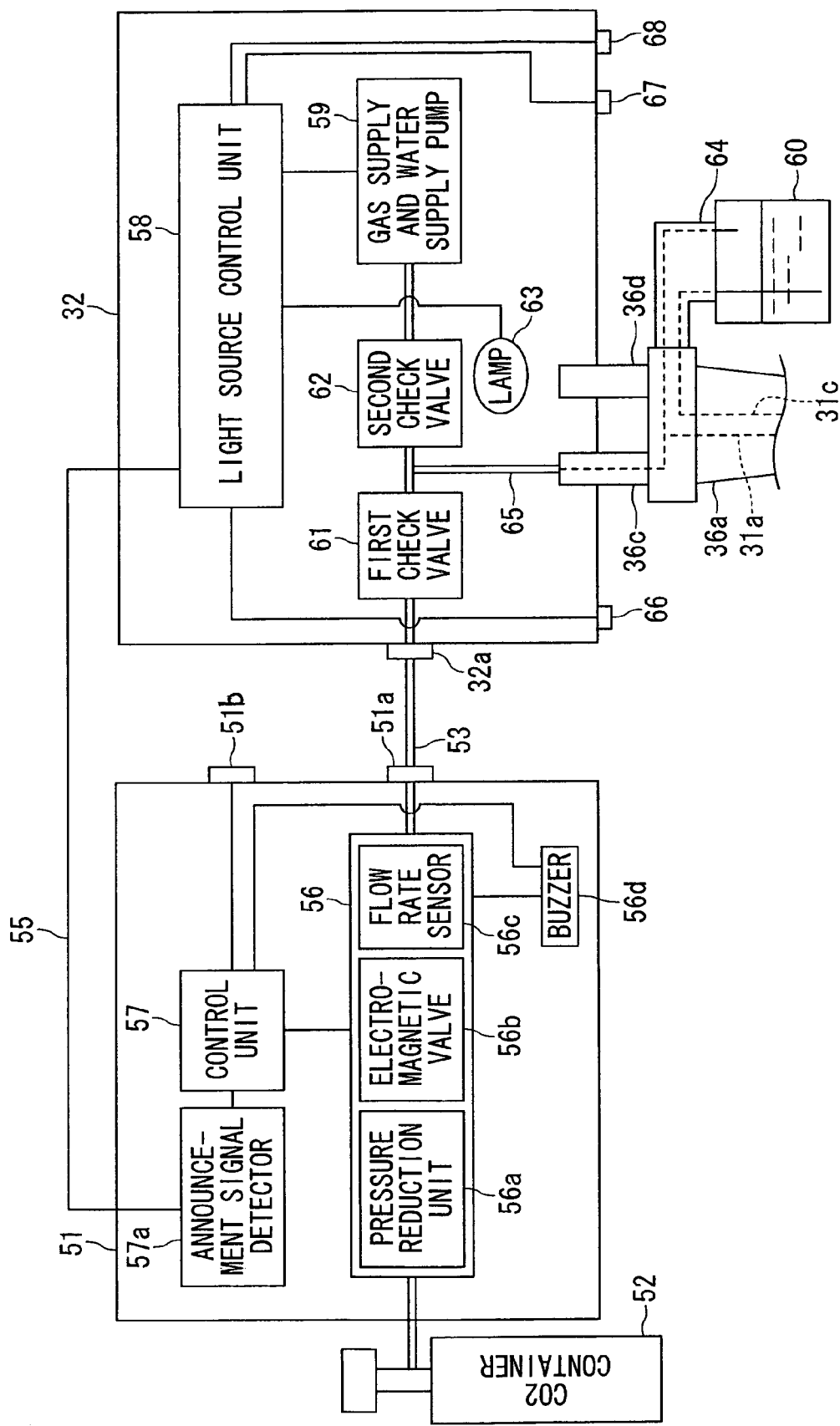
FIG. 2 is a block diagram for illustrating a structure of an ECR and second light source device.

Connecting the endoscope connector 36a to the second light source device 32 allows the light source connector 36d and the illumination lamp 63 to lie in a face-to-face relationship and the gas supply fitting to be brought into communication with a gas supply conduit 65 (see FIG. 2).

Accordingly, the illumination light, irradiated from the illumination lamp 63, is transmitted through a light guide fiber (not shown) and irradiated from an illumination window provided on a distal end, which is not shown, of the inserter section 34.

Further, stored in the water supply tank 60 is liquid such as, for instance, water. Connected to the water supply tank 60 is the water supply tube 64. Air, supplied from the gas supply and water supply pump 59 of the second light source device 32, flows through the gas supply conduit 65 into an upstream gas supply conduit 31a from which air is fed out to the gas supply and water supply button 35a disposed in the manipulator 35. Moreover, at the same time, an interior of the water supply tank 60 is pressurized via a conduit inside the water supply tube 64.

For this reason, upon operation of an operator to manipulate the gas supply and water supply button 35a to allow an upstream water supply conduit 31c and a downstream water supply conduit to be brought into communication with each other, water, fed to the water supply conduit of the endoscope via the water supply tube 64, is injected from a water supply nozzle provided in a distal end, not shown, of the inserter section 34.

The second CCU 33 serves to control a drive of the image pickup element provided on the distal end, which is not shown, of the inserter section 34 of the endoscope 31 and convert the electric signal, resulting from photoelectric conversion of the image focused on the image pickup element, into the image signal. The image signal, converted by the second CCU 33, is outputted to, for instance, the monitor 7 or the centralized display panel 8. This allows the display screen of the monitor 7 or the centralized display panel 8 to be provided with a display of the endoscopic image of the subject taken up by the endoscope 31. Also, reference numeral 39 in FIG. 1 designates an electric cable through which the electric connector 36b, disposed on the endoscope connector 36a, and the second CCU 33 are electrically connected.

The first gas supply apparatus 41, which serves as a system for supplying gas to the abdominal cavity, is mainly comprised of an abdominal insufflation device 41, an abdominal cavity container (hereinafter referred to as a first container) 42 and an abdominal insufflation tube 43. Carbon dioxide gas, serving as abdominal insufflation gas, is stored in the first container 42 in a liquid state.

Disposed on a front panel of the abdominal insufflation device 41 are, for instance, an abdominal insulation coupling 41a and a power switch 41b. Connected to the abdominal insufflation coupling 41a is one end of the abdominal insufflation tube 43, whose other end is connected to the third trocar 16. The power switch 41b is a switch that switches the abdominal insufflation device 41 into an operative state or inoperative state. Operating the power switch 41b to render the abdominal insufflation device 41 operative results in a condition wherein carbon dioxide gas is supplied to the abdominal cavity (i.e., in a carbon dioxide supply state).

The second gas supply apparatus 5, which is a system that supplies predetermined gas, i.e., carbon dioxide gas, to a luminal cavity, is mainly comprised of an endoscopic $CO_2$ regulator (Endoscopic $CO_2$ Regulator: hereinafter abbreviated as ECR) 51, a luminal cavity gas container (hereinafter abbreviated as a second container) 52 in which predetermined observation gas, such as carbon dioxide gas, is stored under a liquid state, and a gas supply tube 53.

Connected to the ECR 51 are a gas supply coupling 51a and a power switch 51b. Connected to the gas supply coupling 51a is one end of the gas supply tube 53, whose other end is connected to the coupling 32a (see FIG. 2) of the second light source device 32. The power switch 51b is a switch that switches the ECR 51 into an operative state or inoperative state. Operating the power switch 51b to render the ECR 51 operative results in a status to allow the ECR 51 to enter a gas supply standby state or a gas supply interruptive state. The tubes 43, 53 are formed of silicon or Teflon (Registered Trademark).

High-pressure gas tubes 44, 54 extending from the first and second containers 42, 52, respectively, are connected to high-pressure fittings, not shown, which are mounted on the abdominal insufflation device 41 and the ECR 51, respectively.

The system controller 6 serves to control operations of a whole surgery operation system 1. Connected to the system controller 5 via communication lines (not shown) in bidirectional communicating capabilities are, in addition to the centralized display panel 8 and the centralized operation panel 9, the electric cautery device 12, the light source devices 22, 32, the CCUs 23, 33 and the abdominal insufflation device 41, all of which serve as peripheral units of the endoscope.

The screen of the monitor 6 receives image signals, outputted form the first CCU 23 or second CCU 33, for providing a display of the endoscopic images of the subject pickup by the rigidscope 21 or the flexiblescope 31.

The centralized display panel 8 is provided with a display screen, such as a liquid crystal display or the like. Connected to the centralized display panel 8 is the system controller 6. Accordingly, the display screen can provide a display of the endoscopic images of the subject as well as the operating statuses on the endoscope peripheral units in a centralized display fashion.

The centralized operation panel 9 is comprised of a display section, such as a liquid crystal display or the like, and a touch sensor section (not shown) integrally formed on a display surface of the display section. The display section of the centralized operation panel 9 has a display function, on which a setting screen, provided with operation switches for various endoscope peripheral units, is displayed, and an operating function by which touching a predetermined area on a particular touch sensor section enables an associated operation switch to be activated.

That is, the centralized operation panel 9 is connected to the system controller 6 and configured to have a capability in that upon suitable operations of the touch sensor section displayed on the display section, various operations or the settings on various operating states can be effectuated for the desired endoscope peripheral units like a manner in which operation switches, provided on the various endoscope peripheral units, respectively, are directly operated. That is, various operations or settings for the endoscopic peripheral units can be performed on the centralized operation panel 9

Mounted on the cart 10a as the various endoscope peripheral units, respectively, are the electric cautery 12, the light source devices 22, 32, the CCUs 23, 33, the abdominal insufflation device 41, the system controller 6, the centralized display panel 8, the centralized operation panel 9 and the first container 42, etc.

Now, a structure and relationship between the ECR 51 and the second light source device 32 are described below.

As shown in FIG. 2, the ECR 51 is comprised of a valve unit 56 and a luminal cavity gas supply control unit 57 serving as a control means. The valve unit 56 includes, for instance, a pressure reduction unit 56a, an electromagnetic valve 56b, which serves as a gas supply changeover unit, and a flow rate sensor 56c serving as a flow rate measuring unit. Reference numeral 56d designates a buzzer. The buzzer 56d is electrically connected to the luminal cavity gas supply control unit 57 serving as the control means.

Connected to the luminal cavity gas supply control unit 57 is an announcement signal detector 57a that serves as detection means. The luminal cavity gas supply control unit 57 has a structure that is comprised of for example a computer, incorporating therein a CPU, which serves as a computing unit, a variety of memories and timers, which sequentially executes a control process based on programs (see FIG. 3 described below), preliminarily stored in predetermined memories, for a luminal cavity gas supply control. Electrically connected to the luminal cavity gas supply control unit 57 is the power switch 1b.

Further, the announcement signal detector 57a is a detector that operates in close cooperation with the luminal cavity gas supply control unit 57, mentioned above, and detects a status signal delivered from the second light source device 32 for the luminal cavity gas supply control. That is, the announcement signal detector 57a, electrically connected to a light source control unit 58, is provided in the second light source device 32, which serves as an illumination status announcement output means, and receives a signal from the control unit 58. Although the announcement signal detector 57a can be realized as a part of a function of the luminal cavity gas supply control unit 57, the control unit 57 may be structured as a separate circuitry.

When rendering the ECR 51 operative, the electromagnetic valve 56b is rendered inoperative in a closed state, that is, in a gas supply interruptive state. Under circumstances where it is detected by the flow rate sensor 56c that no carbon dioxide gas is supplied from the ECR 51, the buzzer 56d is activated to provide such an announcement.

In the meanwhile, provided in the second light source device 32, as shown in FIG. 2, are the light source control unit 58, the gas supply and water supply pump 59, a first check valve 61, a second check valve 62 and the illumination lamp 63. Connected to the light source control unit 58 are the gas supply and water supply pump 59 and the illumination lamp 63.

The gas supply and water supply pump 59 is a pump for injecting gas, such as air or the like, or liquid such as water or the like via the nozzle (not shown) provided in the distal end of the inserter section of the endoscope 31.

The first check valve 61 forms a one-way flow passage through which carbon dioxide gas, supplied from the ECR 51, is introduced to the gas delivery member 65. The second check valve 62 forms a one-way flow passage through which air, supplied from the gas supply and water supply pump 59, is introduced to the gas delivery member 65. The illumination lamp 63 supplies an illumination light of the endoscope 31. The illumination lamp 63 is placed in a face-to-face relationship with an end face of the light source connector 36d.

Included in the display panel of the second light source device 32 are a light source switch 66, a lamp switch 67 and a pump switch 68. The light source switch 66, the lamp switch 67 and the pump switch 68 are electrically connected to the light source control unit 58. Signals are outputted from these switches to the light source control unit 58 whereby upon execution of controls of the control unit 58, switching operations can be effectuated on predetermined objects, respectively.

The light source switch 66 is a switch for switching the second light source device 32 into an operative state or an inoperative state. Operating the light source switch 66 allows LED lamps or the like, which are not shown, of the display panel to light up. The lamp switch 67 is a switch for switching the illumination lamp 63 into a turn-on state or a turn-off state. Operating the lamp switch 67 to light up status the illumination lamp provides a status wherein the illumination light can be transmitted through the endoscope 31 for enabling endoscopic observation. The pump switch 68 is a switch for switching the gas supply and water supply pump 59 in an operative or an inoperative state. Operating the pump switch 68 to drive the gas supply and water supply pump 59 enables air or water to be injected from the above-described nozzle depending on operations of the gas supply and water supply button 35a at hand.

With the second light source device 32 rendered operative, the light source control unit 58 is arranged to output an illumination signal, serving as an operation control signal, which serves as an announcement signal announcing to the announcement signal detector 57a that the illumination lamp 63 is lighted up, and a gas supply and water supply signal as an operation control signal that serves as an announcement signal announcing that the gas supply and water supply pump 59 remains in the operative state.

Under an operative state of the ECR 51, if confirmation is made that only the illumination signal is inputted from the light source control unit 58 to the announcement signal detector 57a, the luminal cavity gas supply control unit 57 delivers a gas supply signal to the valve unit 56. This allows the electromagnet valve 56b to be switched from the closed state to the open state and carbon dioxide gas is supplied from the second container 52 to the second light source device 32 via the ECR 51 (in a gas supply state). As the ECR 51 commences to supply gas, the buzzer 56d intermittently generates announcement sounds such as, for instance, electronic sounds. This results in a capability for users to respond to the sounding of the buzzer 56d for recognizing a condition that carbon dioxide gas is supplied to the endoscope 31.

In contrast, the luminal cavity gas supply control unit 57 cannot confirm that the illumination signal is continuously inputted to the announcement signal detector 57a, or the input of the gas supply and water supply signal can be confirmed, the luminal cavity gas supply control unit 57 closes the electromagnetic valve 56b, thereby interrupting the supply of gas (in a gas supply interruptive state).

Now, description is made of a control of supplying carbon dioxide gas to a luminal cavity with the ECR 51 provided in the surgery operation system 1 with the structure set forth above.

Figure 3:
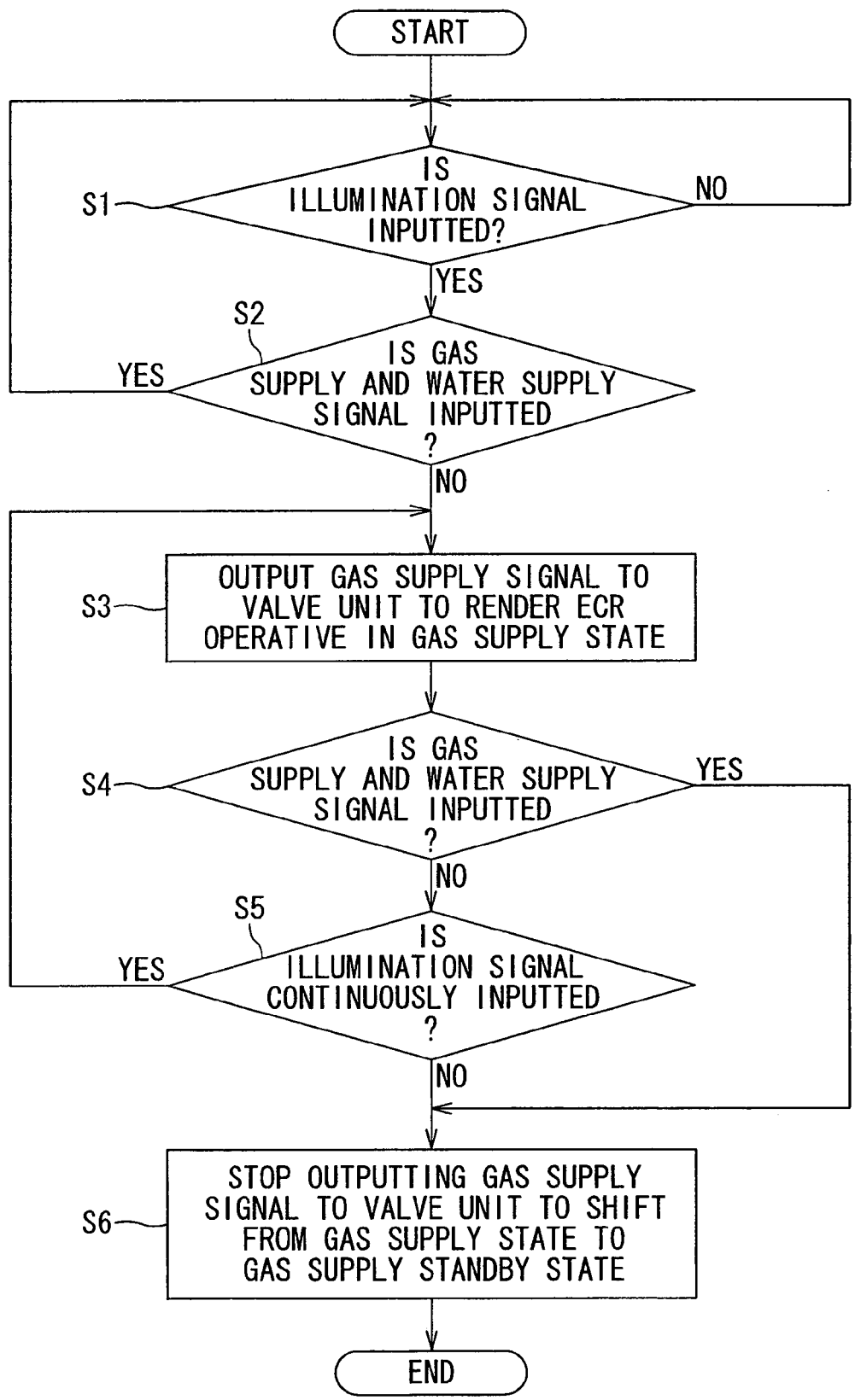
FIG. 3 is a flowchart for illustrating exemplary control for switching the ECR from a gas supply state to a gas supply standby state.

The luminal cavity gas supply control unit 57 of the ECR 51 of the presently filed embodiment executes the operations along a sequence schematically shown in FIG. 3 followed by startup of the luminal cavity gas supply control unit 57. That is, the luminal cavity gas supply control unit 57 confirms whether or not the illumination signal, outputted from the light source control unit 58 provided in the second light source device 32, is inputted to the announcement signal detector 57a (step S1 in FIG. 3). In this moment, if no confirmation is made that the illumination signal is inputted to the announcement signal detector 57a, the luminal cavity gas supply control unit 57 renders ECR 51 to be maintained in a gas supply standby state as an initial state. That is, the electromagnetic valve 56b is maintained in the closed state.

In the meantime, if in step S1, confirmation is made that the illumination signal is inputted, then, the operation proceeds to step S2. In step S2, the luminal cavity gas supply control unit 57 confirms whether or not the gas supply and water supply signal is inputted from the light source control unit 58 to the announcement signal detector 57a. If it is confirmed by the luminal cavity gas supply control unit 57 that the gas supply and water supply signal is inputted to the announcement signal detector 57a, the luminal cavity gas supply control unit 57 maintains the gas supply standby state as the initial state in a manner similar to that set forth above.

On the contrary, if no confirmation is made in step S2 that the gas supply and water supply signal is inputted, then, the operation proceeds to step S3. In step S3, the luminal cavity gas supply control unit 57 outputs a gas supply signal to the valve unit 56. This allows the electromagnetic valve 56b to be switched from the closed state to the open state, resulting in the gas supply state to allow carbon dioxide gas to be supplied from the second container 52 to the second light source device 32 via the ECR 51. When this takes place, the buzzer 56d is activated to intermittently generate the electronic sounds. This enables the operator to recognize a status in which carbon dioxide gas is being supplied to the endoscope 31 from the ECR 51.

Upon commanding such a gas supply state, carbon dioxide gas, supplied from the ECR 51, is supplied to the gas supply fitting 36c via a gas supply tube 53, the first check valve 61 and a delivery member 65. Carbon dioxide gas, supplied to the gas supply fitting 36c, flows through the upstream gas supply conduit 31a into a gas supply and water supply button cylinder (hereinafter abbreviated as a gas supply and water supply cylinder) 35c that incorporates a gas supply and water supply button 35a provided on the manipulator 35.

Figure 5:
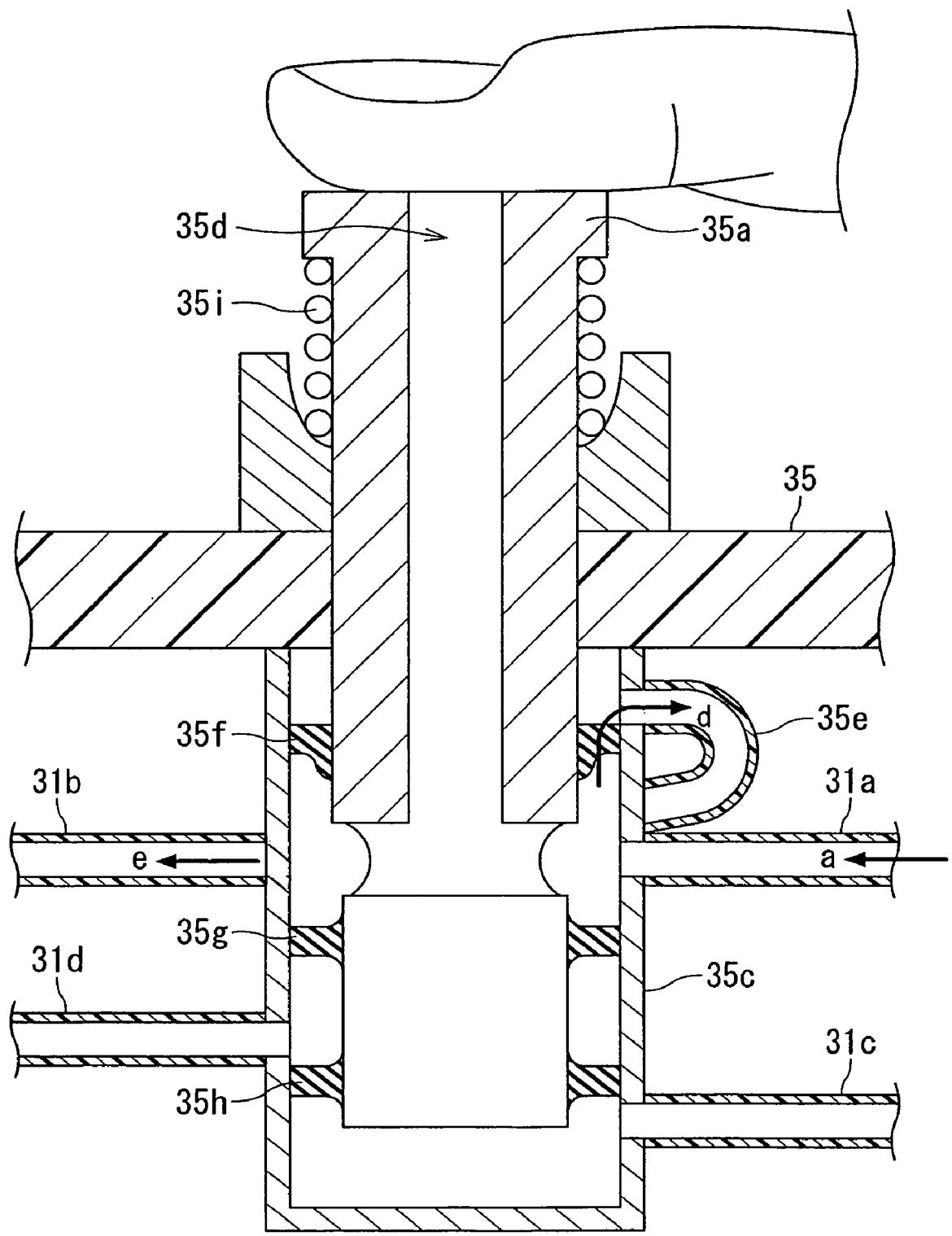
FIG. 5 is a view for illustrating a condition under which the bore portion, formed in the gas supply and water supply button, is blocked to allow carbon dioxide gas to be supplied to an inserter section.

Here, the presence of a bore portion 35a, formed in the gas supply and water supply button 35a, left in an open state results in a gas leakage state wherein carbon dioxide gas belches out of the bore portion 35d in a path as shown by arrows "a", "b", and "c" in the drawing figure. In contrast, if the bore portion 35d, formed in the gas supply and water supply button 35a, is blocked by an operator's finger as shown in FIG. 5, carbon dioxide gas, supplied through the upstream gas supply conduit 31a, is supplied to the downstream gas supply conduit 31b via a bent pipe 35e in a path as shown by arrows "a", "d", and "e" in the drawing figure without leaking to the outside from the bore portion 35d. This results in a "luminal-cavity carbon dioxide gas supply state" in which carbon dioxide gas is supplied to the luminal cavity via the nozzle.

Figure 4:
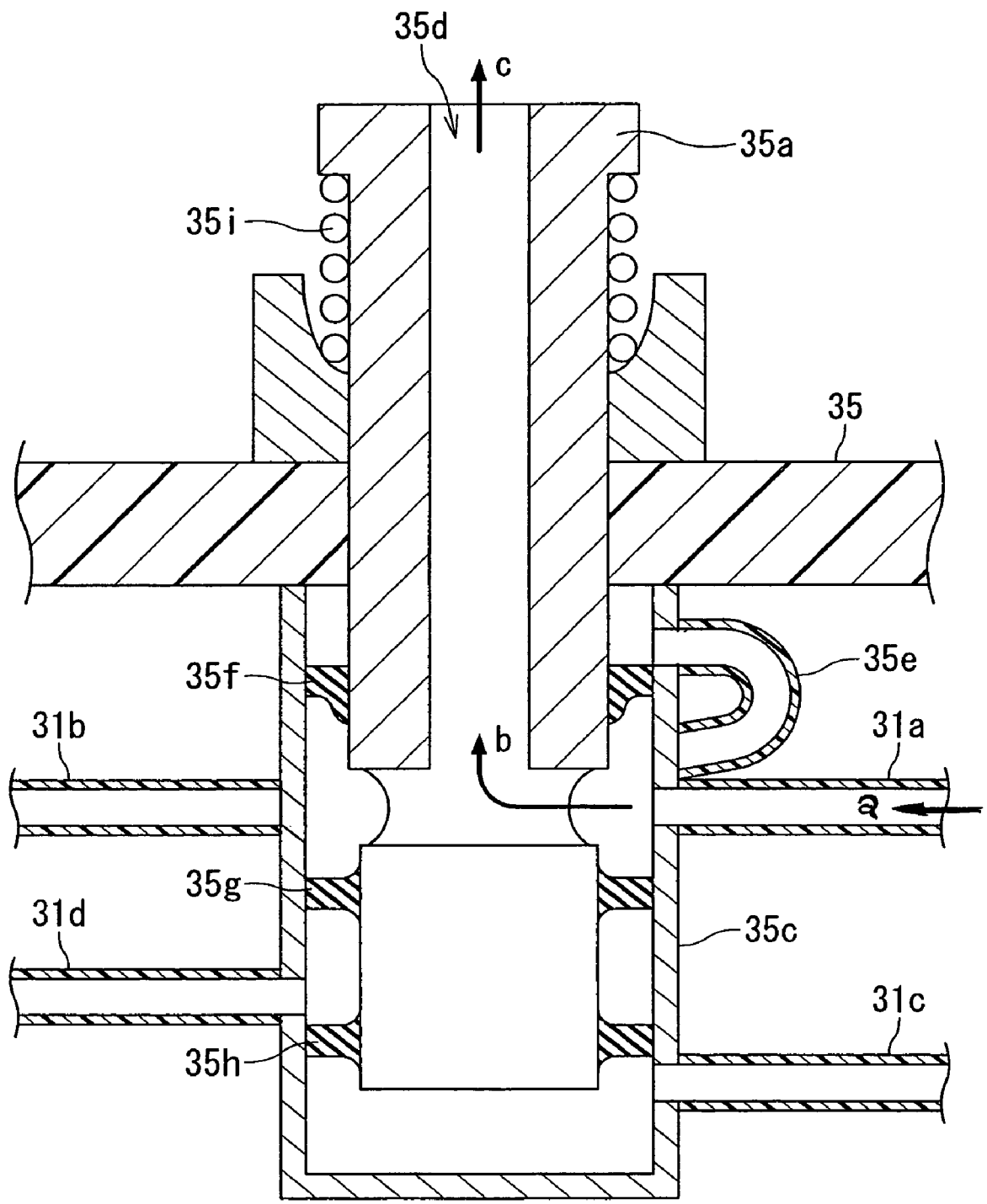
FIG. 4 is a view for illustrating a leaked condition under which carbon dioxide gas belches from a bore portion formed in a gas supply and water supply button.

Also, in FIGS. 4 and 5, reference numeral 31c designates an upstream water supply conduit; reference numeral 31d designates a downstream water supply conduit; reference numeral 35f designates a check valve; reference numerals 35g and 35h designate gaskets; and reference numeral 35i designates a spring.

Further, under a condition shown in FIG. 5, as the gas supply and water supply button 35a is pressed down by a predetermined stroke against the force of the spring 35i, the check valve 35f and the gaskets 31g, 35h are moved downward in position to allow the upstream gas supply conduit 31c and the downstream water supply conduit 31d to be brought into communication with each other.

As set forth above, if the gas supply state as shown in step S3 is present, the luminal cavity gas supply control unit 57 confirms whether or not the gas supply and water supply signal is inputted from the light source control unit 58 to the announcement signal detector 57a (step S4 in FIG. 3). Upon a result of such confirmation, if the luminal cavity gas supply control unit 57 does not confirm that the gas supply and water supply signal is inputted to the announcement signal detector 57a, the operation proceeds to step S5. In step S5, the luminal cavity gas supply control unit 57 confirms whether or not the illumination signal is continuously inputted to the announcement signal detector 57a. As a result of such confirmation, if the luminal cavity gas supply control unit 57 confirms that the illumination signal is inputted to the announcement signal detector 57a, the operation proceeds to step S3 to maintain the operation in the gas supply state.

In the meantime, if in step S4, the luminal cavity gas supply control unit 57 is able to confirm that the gas supply and water supply signal is inputted to the announcement signal detector 57a, or if the luminal cavity gas supply control unit 57 cannot confirm that the illumination signal is inputted to the announcement signal detector 57a, the operation proceeds to step S6.

In step S6, the luminal cavity gas supply control unit 57 stops outputting the gas supply signal to the valve unit 56. In response to such operation, the electromagnetic valve 56b is switched from the open state to the closed state. This stops supplying carbon dioxide gas from the second container 52 to the second light source device 32 and subsequently interrupting the buzzer 56d from generating the sounds.

Also, while the presently filed embodiment utilizes a mode of generating the sounds for providing an announcement to the operator to indicate the presence of a condition in that carbon dioxide gas is being supplied from the ECR 51 to the endoscope 31, an alternative may be configured such that, for instance, the display panel is provided with a display of characters "On Supply of Carbon Dioxide Gas to Luminal cavity" or a display in a flashing state for thereby announcing the state in which carbon dioxide gas is being supplied to the endoscope 31.

In such a way, the presently filed embodiment takes the form of a structure in which under a condition where the second light source device and the ECR are connected through the communication cable and the illumination lamp, provided in the second light source device, is light up, the light source device control unit of the second light source device outputs the illumination signal and the gas supply and water supply signal to the announcement signal detector of the ECR. Therefore, the luminal cavity gas supply control unit confirms the presence of or absence of the illumination signal and the presence of or absence of gas supply and water supply signal, applied to the announcement signal detector, enabling a control to switch the ECR between the gas supply state and the gas supply interruptive state.

Although this allows the ECR to enter the gas supply state under a condition where, after the ECR has been shifted to the operative state, the second endoscope outputs the illumination signal to the ECR, the ECR enters the gas supply interruptive state during a condition where the output of the illumination signal is interrupted or the gas supply and water supply signal is outputted.

Accordingly, if a medical service worker operates the light source device switch or the lamp switch for turning off the light source device lamp, the ECR enters the gas supply interruptive state in conjunction with the turnoff operation of the light source device lamp, thereby reliably preventing wasteful consumption of carbon dioxide gas from the second container connected to the ECR during off-periods of endoscopic observation.

Second Embodiment

Figure 6:
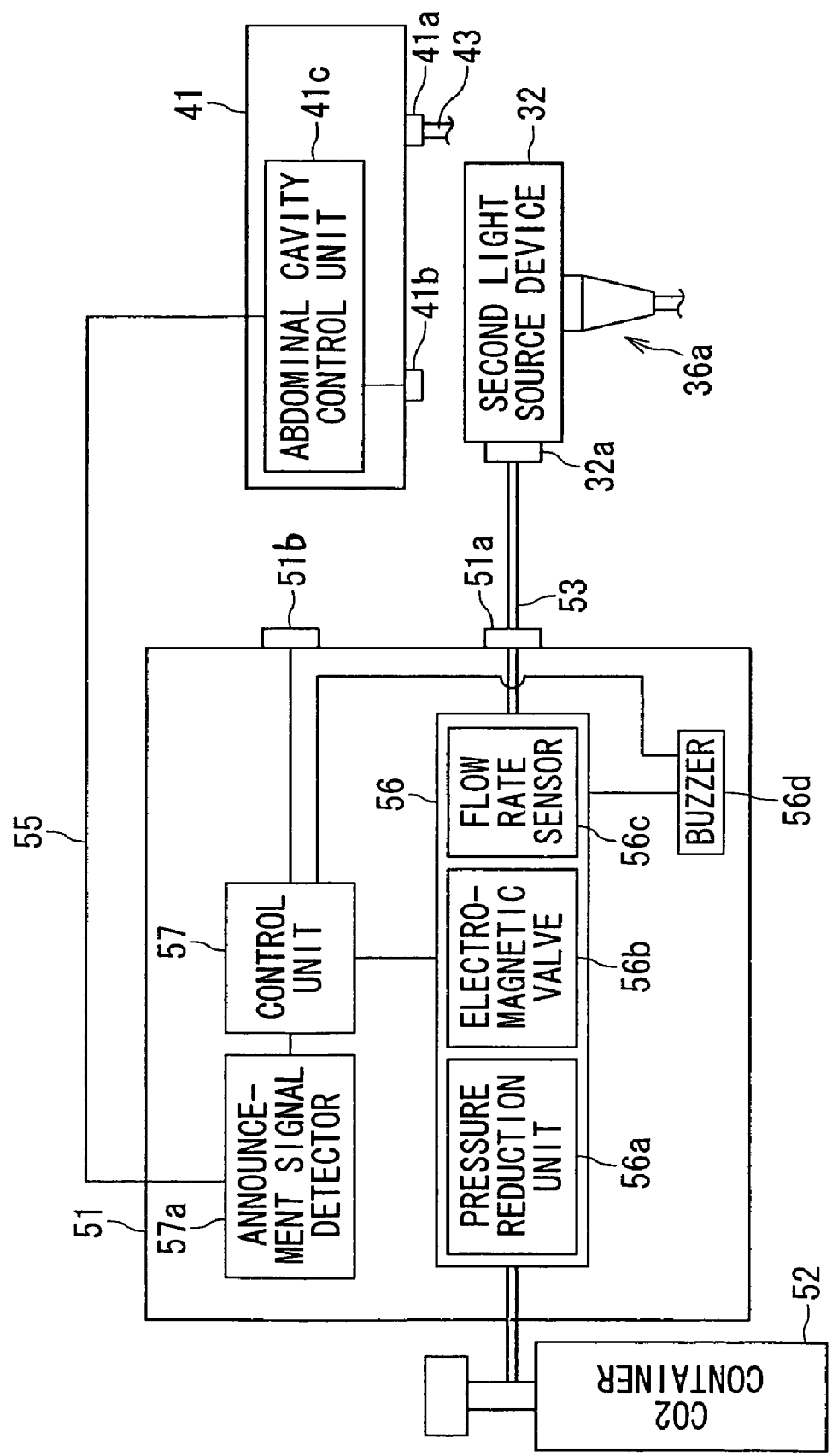
FIG. 6 is a block diagram illustrating the relationship among an ECR, a second light source device and an abdominal insufflation device of an endoscopic system of a second embodiment according to the present invention.
Figure 7:
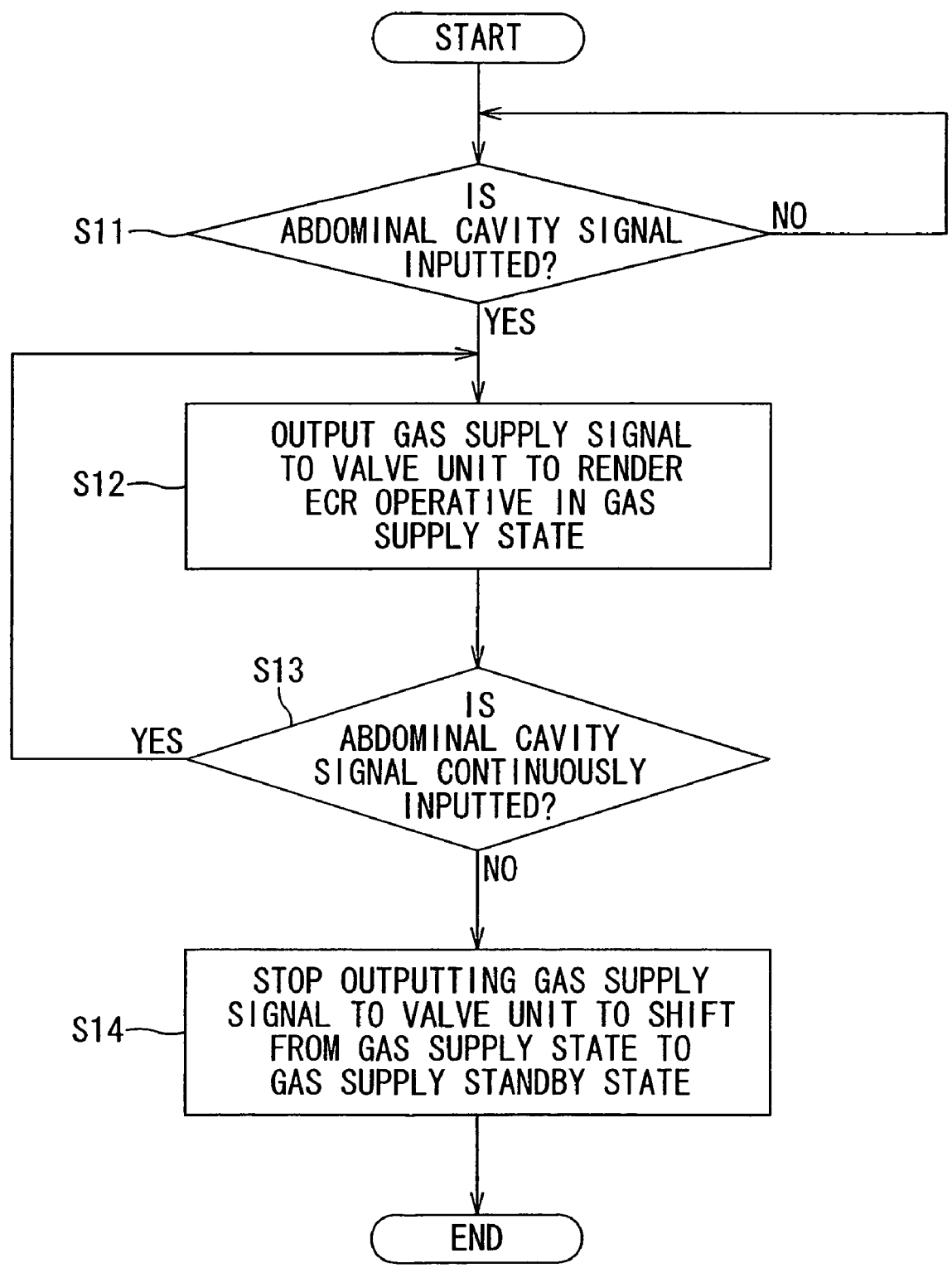
FIG. 7 is a flowchart illustrating exemplary control of confirming whether or not the abdominal insufflation device is rendered operative to switch the ECR into a gas supply state and a gas supply standby state.

Referring to FIGS. 6 and 7, an endoscopic system, equipped with the gas supply apparatus, of a second embodiment according to the present invention is described.

With the present embodiment, in place of electrically connecting the second light source device 32 and the ECR 51 through the communication cable 55, the abdominal insufflation device 41 and the ECR 51 are electrically connected through the communication cable 55. In addition, the presently filed embodiment takes the form of a structure wherein during a condition in which the abdominal insufflation device 41 is rendered operative, an abdominal cavity control unit 41c, provided in the abdominal insufflation device 41 and serving as a signal output means, outputs an abdominal cavity signal as an operation control signal, which serves as an announcement signal indicative of the abdominal insufflation device 41 remaining under the operative state, to the announcement signal detector 57a provided in the ECR 51. Other structures are similar to those of the first embodiment and, therefore, the same component parts bear like reference numerals to omit redundant description.

With such a structure, when the ECR 51 is rendered operative, the luminal cavity gas supply control unit 57 confirms whether or not the abdominal cavity signal, outputted from the abdominal cavity control unit 41c provided in the abdominal insufflation device 41, is inputted to the announcement signal detector 57a. In this moment, if the luminal cavity gas supply control unit 57 does not confirm that the abdominal cavity signal is inputted to the announcement signal detector 57a, the ECR 51 is sustained in a gas supply standby state.

On the contrary, if the luminal cavity gas supply control unit 57 confirms in step S11 that the abdominal cavity signal is inputted to the announcement signal detector 57a, the operation proceeds to step S12. In step S12, the luminal cavity gas supply control unit 57 outputs the gas supply signal to the gas valve unit 56. This allows the electromagnetic valve 56b to be rendered operative to shift from the closed state to the open state. This results in the gas supply state under which carbon dioxide gas is supplied from the second gas container 52 to the second light source device 32 via the ECR 51. When this takes place, the buzzer 56d is activated to intermittently generate the electronic sounds.

With the gas supply state shown in step S12 appeared, the luminal cavity gas supply control unit 57 confirms in step S13 whether or not the abdominal cavity signal is continuously inputted to the announcement signal detector 57a. In this moment, if the luminal cavity gas supply control unit 57 confirms that the abdominal cavity signal is inputted to the announcement signal detector 57a, the operation proceeds to step S12 upon which a gas supply state is sustained.

On the contrary, if the luminal cavity gas supply control unit 57 cannot confirm in step S13 that the abdominal cavity signal is inputted to the announcement signal detector 57a, the operation proceeds to step S14. In this step S14, the luminal cavity gas supply control unit 57 interrupts outputting of the gas supply signal to the valve unit 56. In response to this, the electromagnetic valve 56b is rendered inoperative, which shifts from the open state to the closed state, thereby interrupting the supply of carbon dioxide gas from the second gas container 52 to the second light source device 32 via the ECR 51, upon which the buzzer 56d is deactivated to stop generating the sounds.

Thus, with the abdominal insufflation device and ECR electrically connected, the luminal cavity gas supply control unit executes the operation to confirm the presence of or absence of the abdominal cavity signal outputted from the abdominal insufflation device to the announcement signal detector, enabling the execution of control to switch the ECR between the gas supply state and the gas supply interruptive state.

By so doing, after the surgical operation, executed upon supplying carbon dioxide gas to the abdominal cavity, is terminated, the power switch of the abdominal insufflation device is turned off to shift into a drive interruptive state and, in association with such an operation, the electromagnetic valve, provided in the ECR, is rendered inoperative to shift into the closed state. This results in a capability of reliably preventing carbon dioxide gas from wastefully consuming from the second gas container after the operation has been terminated.

Also, the system controller 6 of the presently filed embodiment is connected to the centralized display panel 8, the centralized operation panel 9, the electric cautery device 12, the light source devices 22, 32, the CCUs 23, 33 and the abdominal insufflation device 41, all of which serve as the endoscopic peripheral units, respectively, through a communication line (not shown) with bidirectional communication capabilities. Therefore, connecting the ECR 51 to the system controller 6 through a communication line (not shown) results in a structure that is enabled to execute a control of the surgery operation system 1 as a whole in a lump sum.

That is, the light source control unit 58 of the second light source device 32 and the announcement signal detector 57a provided in the ECR 51 can be electrically connected or the abdominal cavity control unit 41c of the abdominal insufflation device 41 and the announcement signal detector 57a provided in the ECR 51 can be electrically connected without causing a need for the second light source device 32 and the ECR 51 to be connected through the communication cable and the abdominal insufflation device 41 and the ECR 51 to be connected through the communication cable.

With such a structure, the illumination signal and the gas supply and water supply signal, outputted from the second light source device 32, and the abdominal cavity signal, outputted from the abdominal insufflation device 41 can be transmitted to the announcement signal detector 57a of the ECR 51 via the control unit (not shown) provided in the system controller 6. Therefore, no communication cable 55 is needed and work for connecting the communication cables can be dispensed with.

Figure 8:
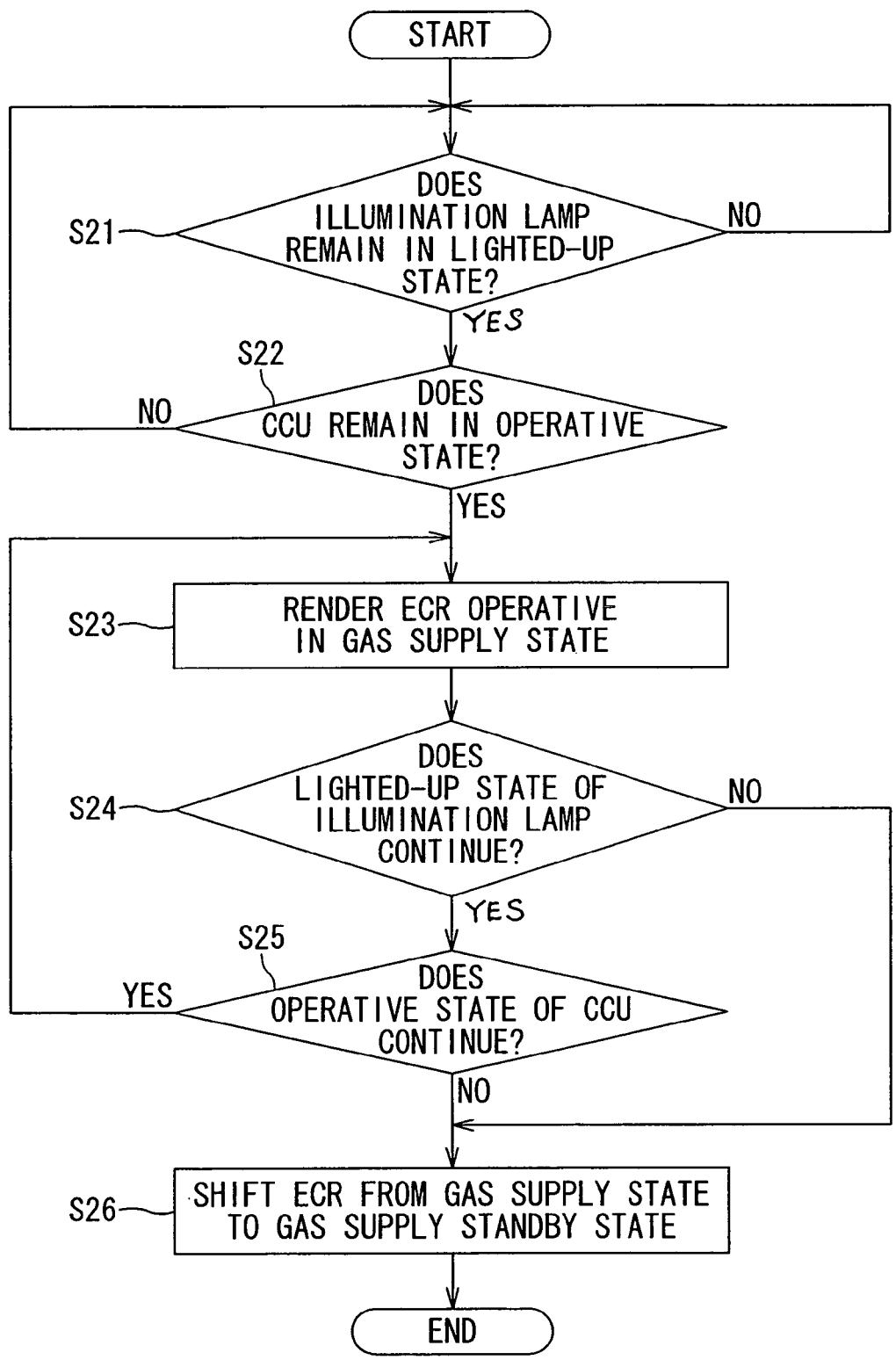
FIG. 8 is a flowchart illustrating exemplary control, in a modified form of the second embodiment, for confirming whether or not an illumination lamp remains in a turn-on state and the abdominal insufflation device is rendered operative to switch the ECR into the gas supply state and the gas supply standby state.

A modified form is shown in FIG. 8.

FIG. 8 is a flowchart for illustrating a basic sequence of operations in an exemplary control of executing confirmation whether or not the illumination lamp lies in the light up status and whether or not the CCU remains in the operative state upon which the ECR is switched to a gas supply state or gas supply standby state.

With the structure incorporating the system controller 6 to control the surgery operation system 1 as a whole in a lump sum, the ECR 51 may be configured in structure to control the gas supply state or the gas supply interruptive state via the system controller 6 upon confirming, as shown in FIG. 8, whether or not the second light source device 32 and the second CCU 33 remain in the respective operative states.

With the ECR 51 rendered operative, in step S21 shown in FIG. 8, initially, the system controller 6 confirms whether or not the illumination lamp 63, disposed in the light source device 32, remains in the light up status. In this moment, if the system controller 6 confirms that the illumination lamp 63 remains in the turnoff status, the gas supply standby state is sustained.

In contrast, in step S21, if the light up status of the illumination lamp 63 is confirmed, the operation proceeds to step S22. In step S22, the system controller 6 confirms whether or not the second CCU 33 lies in the operative state. In this moment, if the system controller 6 confirms that the second CCU 33 lies under an inoperative state, the operation proceeds to step S21 upon which the gas supply standby state is sustained.

In the meanwhile, in step S22, if the system controller 6 confirms that the second CCU 33 lies in the operative state, the operation proceeds to step S23. In step S23, the system controller 6 outputs a gas supply signal to the valve unit 56 via the luminal cavity gas supply control unit 57. By so doing, the electromagnetic valve 56b is rendered operative to shift from the closed state to the open state resulting in the gas supply state under which carbon dioxide gas is supplied from the second container 52 to the second light source device 32 via the ECR 51 while the electronic sounds are generated.

With the ECR 51 entered in the gas supply state shown in step S23, as shown in step S24, the system controller 6 confirms whether or not the light up status of the second illumination source 32 is sustained. In this moment, if the system controller 6 confirms that the light up status is sustained, the operation proceeds to step S25. In step S25, the system controller 6 confirms whether or not the operative status of the second CCU 33 is continuously sustained. In this moment, if the system controller 6 confirms that the second CCU 33 remains operative, the operation proceeds to step S23 upon which the gas supply state is sustained.

In contrast, if the system controller 6 confirms in step S24 that the second light source device 32 lies in the turnoff state or if the system control section confirms in step S25 that the second CCU 33 remains in the inoperative state, the operation proceeds to step S26.

In step S26, the system controller 6 causes the luminal cavity gas supply control unit 57 of the ECR 51 to interrupt outputting the gas supply signal to the valve unit 56. In response to such operation, the electromagnetic valve 56b is switched from the open state to the closed state. This results in operation of the ECR 51 to interrupt supplying carbon dioxide gas from the second container 52 to the second light source device 32 after which the buzzer 56d is also deactivated to interrupt generating the sounds.

Thus, with the system controller 6 configured to execute the operation for confirming whether or not the second light source device lies in the operative state and whether or not the second CCU 33 remains in the operative state upon which the control is executed for switching the ECR between the carbon dioxide gas supply state and the gas supply interruptive state, the ECR can be reliably brought into the gas supply interruptive state under a condition wherein no endoscopic observation can be performed through the second endoscope.

With such a configuration, even under a condition with the illumination lamp remaining in the light up state, the second CCU is rendered inoperative thereby disenabling observation through the second endoscope and, in association with this, the electromagnetic valve, provided in the ECR, is rendered inoperative in the closed state, thereby reliably preventing carbon dioxide gas from being wastefully consumed from the gas container. In addition, in executing the endoscopic observation, even under a condition wherein the illumination lamp is lighted up for a time interval of from several tens of seconds to several minutes for the purpose of causing the illumination lamp of the light source device to operate in a stable light emitting state, wasteful consumption of carbon dioxide from the gas container can be reliably prevented.

Third Embodiment

Figure 9:
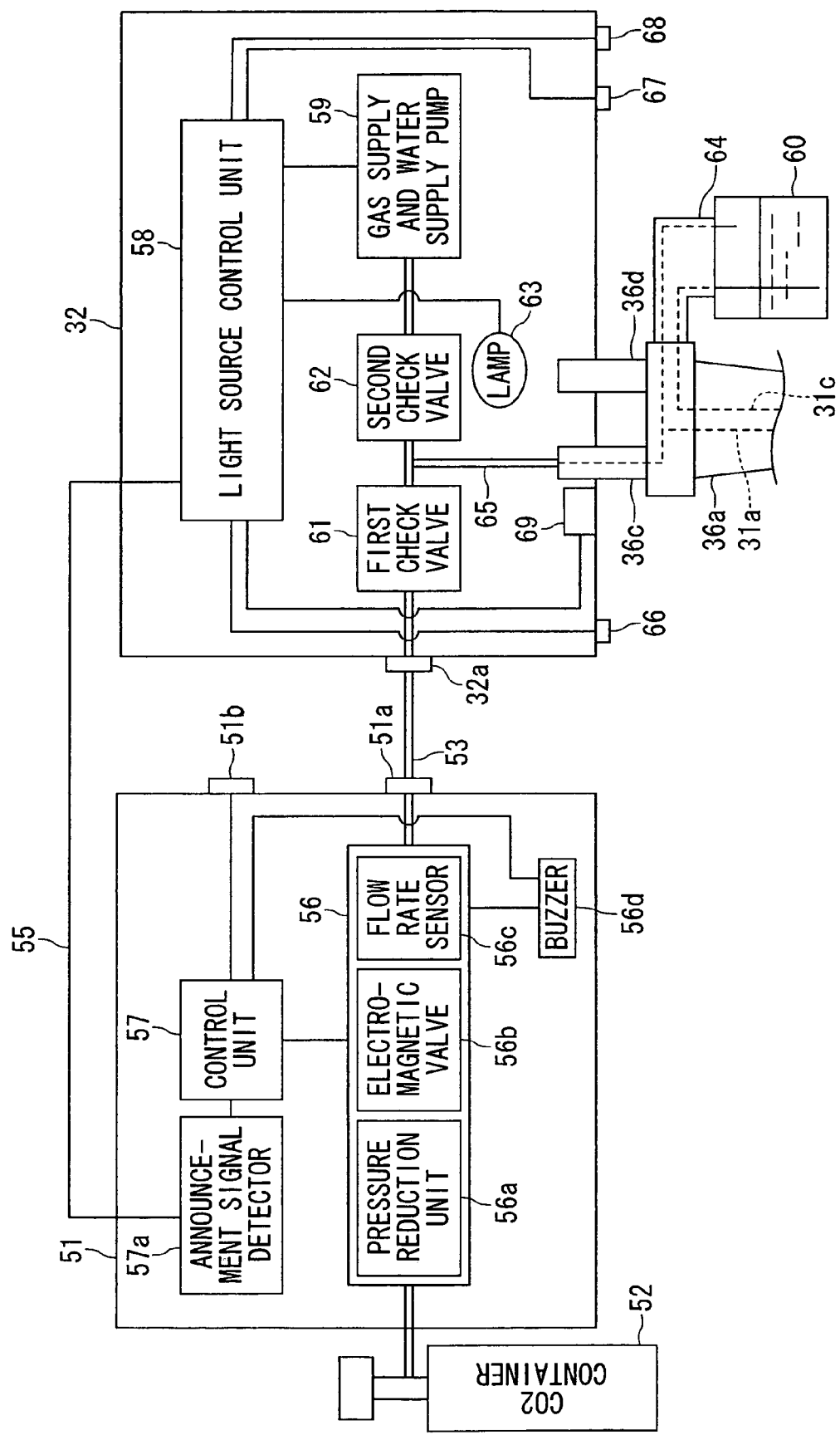
FIG. 9 is a block diagram for illustrating the relationship between an ECR and a second light source device of an endoscopic system of a third embodiment according to the present invention.

Referring to FIG. 9, an endoscopic system, equipped with a gas supply apparatus, of a third embodiment according to the present invention is described.

As shown in FIG. 9, with the present embodiment, the second light source device 32 incorporates a light source connector detection sensor 69, serving as a connection status discriminating unit, which detects whether or not there is a status under which the light source connector 36d is connected to the second light source device 32. The light source connector detection sensor 69 may include a sensor of, for instance, an optical type or contact type and electrically connected to the light source control unit 58. Other structures are similar to those of the first embodiment and the same component parts bear like reference numerals to omit redundant description.

With such a structure of the presently filed embodiment, under a condition where the light source connector 36d is connected to the second light source device 32, the light source connector detection sensor 69 outputs a connector connection signal to the light source control unit 58 indicative of an announcement on the presence of the light source connector 36d remaining in a connected status. Then, upon receipt of the connector connection signal, the light source control unit 58 outputs an endoscope connection signal to the announcement signal detector 57a. This allows the ECR 51 to be switched to the gas supply interruptive state if the light source connector 36d is pulled out of the second light source device 32 during a period in which the ECR 51 remains in the operative state i.e., the carbon dioxide gas supply status.

That is, if the light source connector 36d is pulled out of the second light source device 32, no connector connection signal is outputted from the light source connector detection sensor 69. Therefore, no endoscope connection signal is outputted from the light source control unit 58 to the announcement signal detector 57a. This allows the luminal cavity gas supply control unit 57 of the ECR 51 to interrupt outputting the gas supply signal to the valve unit 56. Depending on such operation, the ECR 51 is switched from the gas supply state to the gas supply interruptive state.

Thus, by switching the electromagnetic valve, provided in the ECR, to the closed state in association with the operation in which the light source connector 36d is pulled out of the second light source device 32, it becomes possible to prevent wasteful consumption of carbon dioxide gas from the gas container during off-periods in endoscopic observation.

Fourth Embodiment

Figure 10:
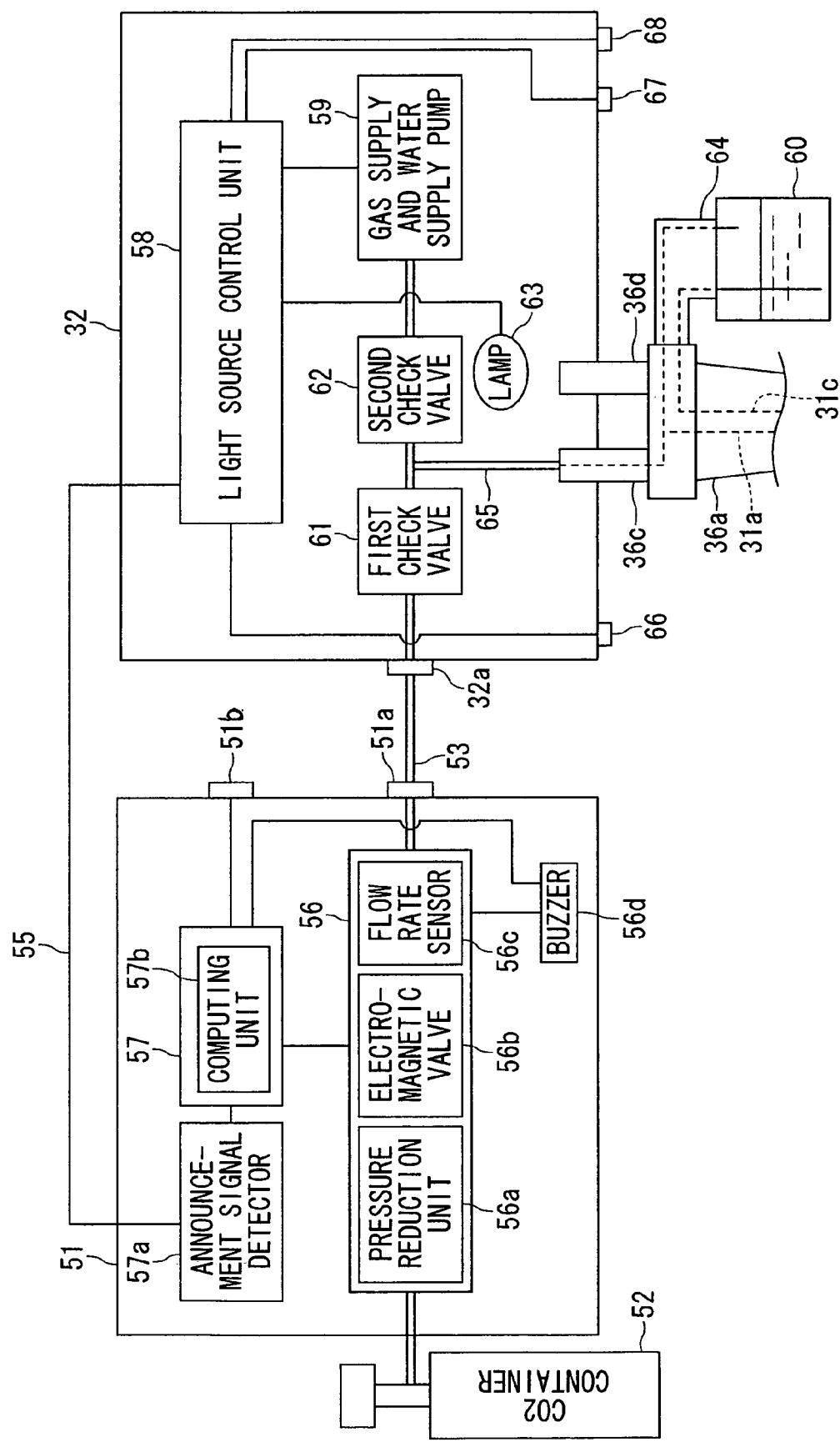
FIG. 10 is a block diagram for illustrating the relationship between an ECR and a second light source device of an endoscopic system of a fourth embodiment according to the present invention.
Figure 11:
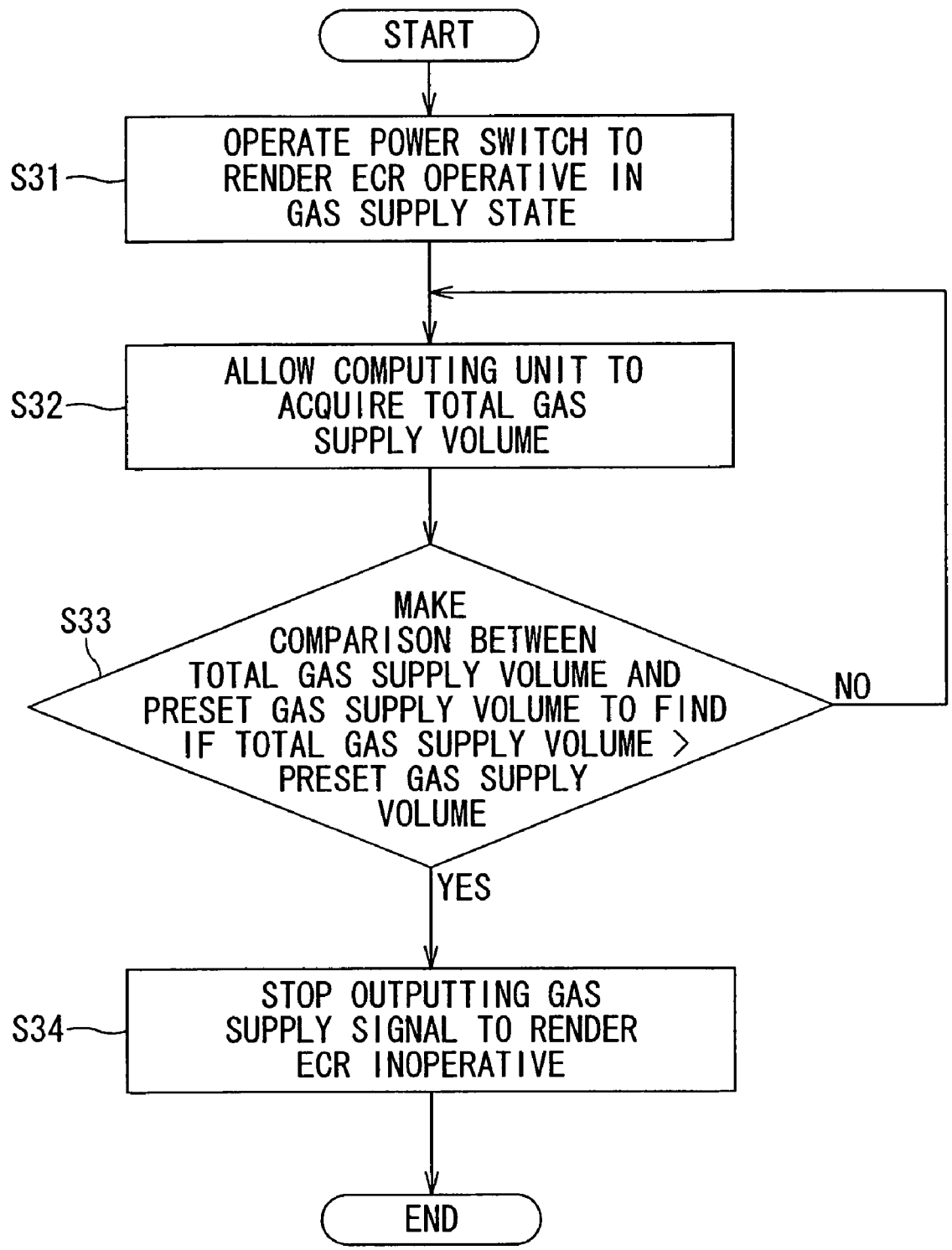
FIG. 11 is a flowchart illustrating exemplary control for switching the ECR in a modified form of the fourth embodiment according to the present invention.

Referring to FIGS. 10 and 11, an endoscopic system, equipped with a gas supply apparatus, of a fourth embodiment according to the present invention is described.

As shown in FIG. 10, with the present embodiment, the luminal cavity gas supply control unit 57 incorporates a computing unit 57b composed of a CPU. The computing unit 57b is applied with a measured flow rate value of carbon dioxide gas passing across the flow rate sensor 56c, thereby allowing a total volume of supplied gas after the ECR 51 has been switched to the gas supply state.

As shown in step S31 in FIG. 11, the power switch 51b is turned on. In response to such turn-on operation, the luminal cavity gas supply control unit 57 outputs a gas supply signal to the valve unit 56. This allows the ECR 51 to enter the gas supply state. Under such a gas supply state, a measured flow rate value of the flow rate sensor 56c is inputted to the computing unit 57b as shown in step S32. Here, the computing unit 57b executes the operation to obtain a total gas supply volume upon executing accumulating operation based on the measured flow rate value that has been inputted.

Next, the operation proceeds to step S33 in which comparison is made between the total gas supply volume, obtained by the computing unit 57b, and a preset gas supply volume that is preliminarily set prior to starting a surgery operation. Here, if the luminal cavity gas supply control unit 57 discriminates that total gas supply volume is less than the preset gas supply volume, then, the operation is routed back to step S32 in which the operation is executed to allow the ECR 51 to be sustained in the operative state, that is, under a status in which gas supply is continued. On the contrary, if the luminal cavity gas supply control unit 57 discriminates that the total gas supply volume exceeds the preset gas supply volume, the operation proceeds to step S34. In step S34, the luminal cavity gas supply control unit 57 interrupts the outputting of the gas supply signal while executing the control to switch the ECR 51 from the operative state to the inoperative state.

Thus, with such a structure wherein a total volume of carbon dioxide gas to be supplied from the ECR to the endoscope is preliminarily set while permitting the computing unit, provided in the ECR, to calculate a total volume of gas supplied after the ECR has entered the gas supply state, the luminal cavity gas supply control unit is enabled to control an operative status of the ECR upon executing comparison between the preset gas volume and the total supplied volume whereby carbon dioxide gas can be reliably prevented from being wastefully consumed from the container.

Also, with the presently filed embodiment, when it is desired to render the ECR to lie in the gas supply state, the power switch 51b is turned on as shown in step S31, thereby rendering the ECR 51 operative. Then, a total volume of gas, to be supplied from the ECR 51, can be suitably preset on, for instance, the centralized operation panel 9 and a preset gas supply volume is displayed on, for instance, the display panel.

Fifth Embodiment

Figure 12:
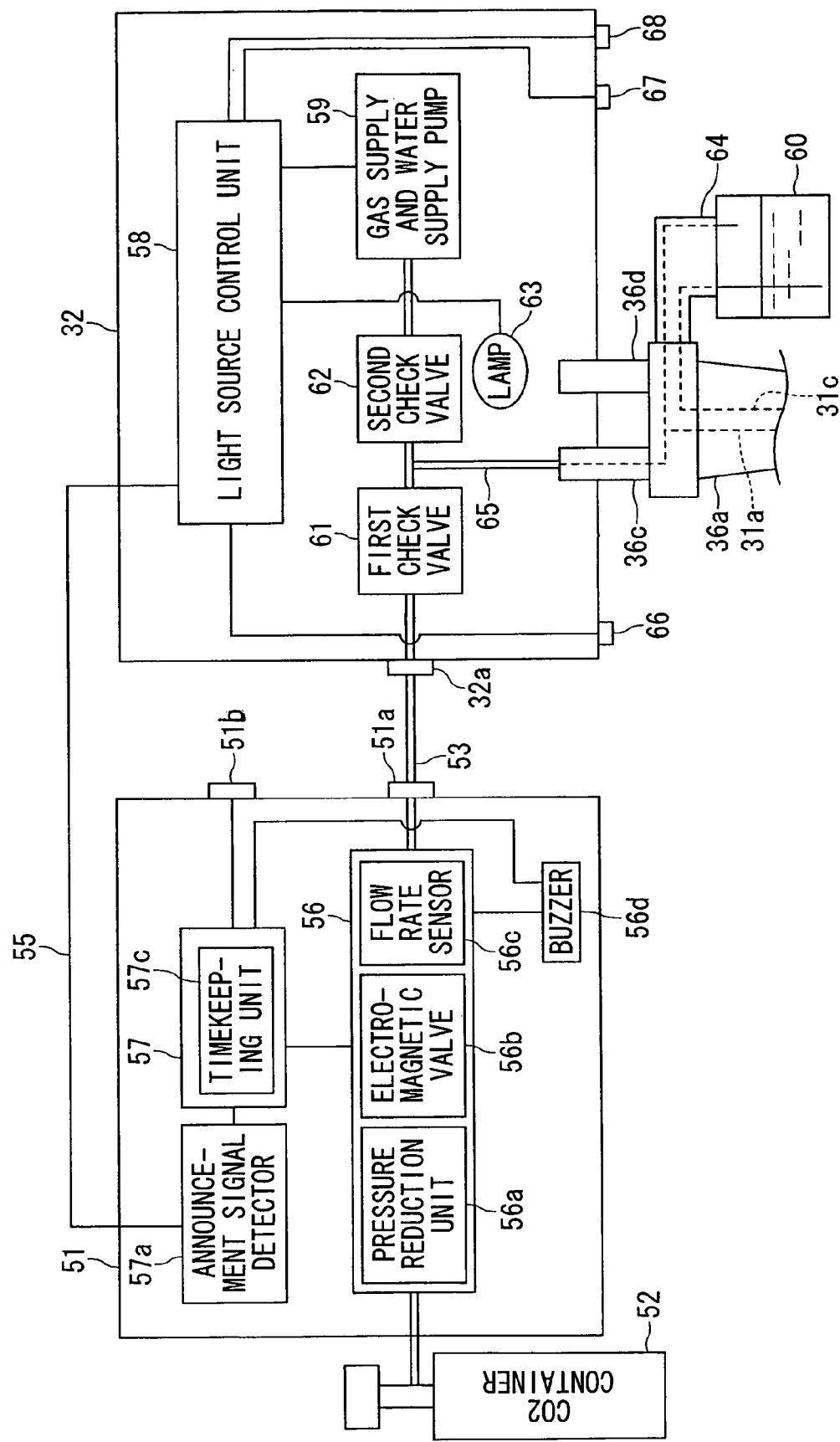
FIG. 12 is a block diagram for illustrating the relationship between an ECR and a second light source device of an endoscopic system of a fifth embodiment according to the present invention.
Figure 13:
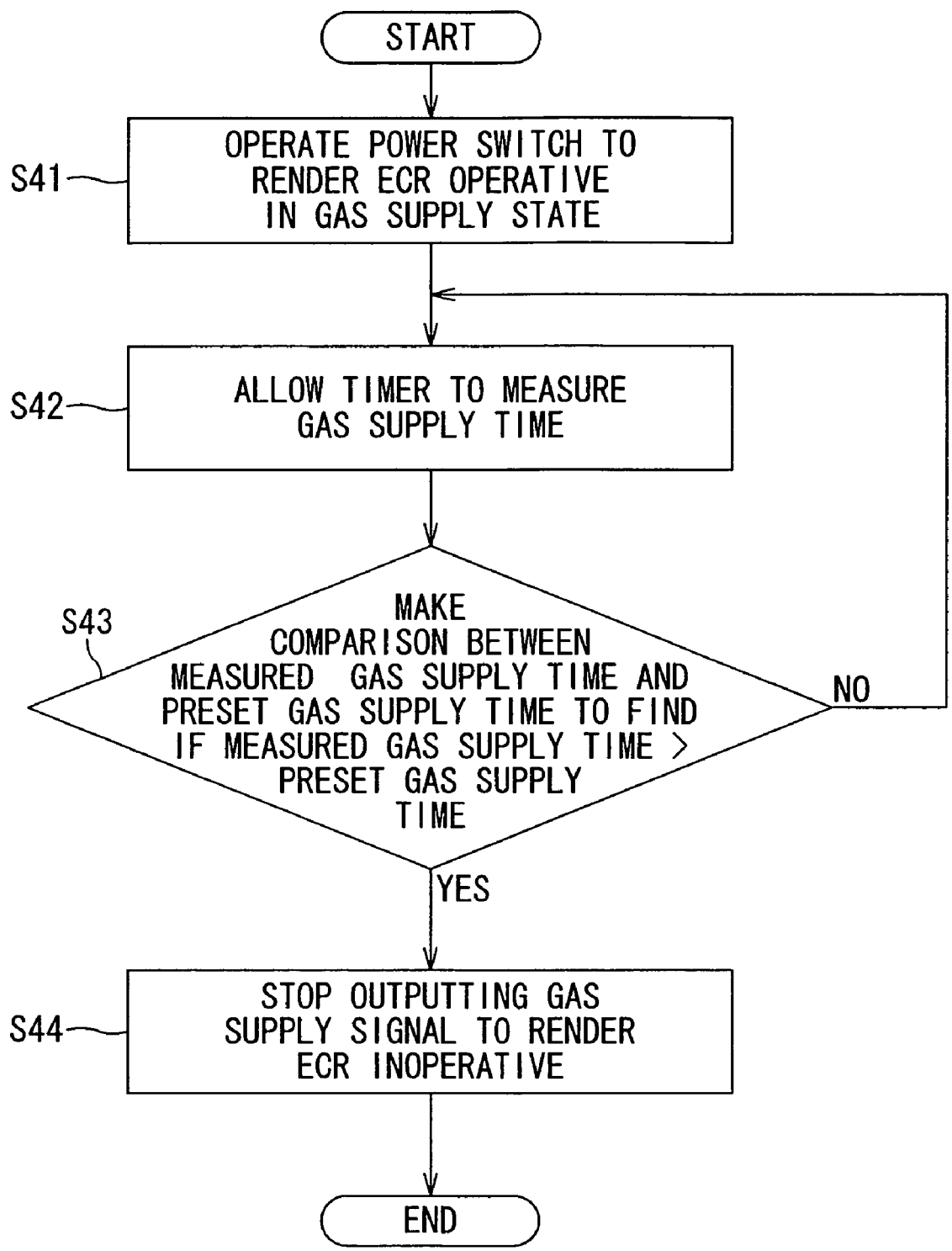
FIG. 13 is a flowchart illustrating exemplary control of switching the ECR, remaining under the gas supply state, to a gas supply stop state.

Referring to FIGS. 12 and 13, an endoscopic system, equipped with a gas supply apparatus, of a fifth embodiment according to the present invention is described.

The present embodiment is configured to perform a luminal cavity gas supply control as a function of a parameter of a gas supply duration in place of the total gas supply volume adopted in the fourth embodiment. That is, in place of the ECR 51 incorporating the computing unit to allow the ECR 51 to be controllably switched from the operative state to the inoperative state upon calculating the total gas supply volume, the luminal cavity gas supply control unit 57 is configured to incorporate a timekeeping unit (also referred to as a timer) 57c, serving as a timekeeping unit, as shown in FIG. 12. The timekeeping unit 57c detects a gas supply duration to execute control for switching the ECR 51 from the operative state to the inoperative state based on a detected gas supply duration.

That is, the timekeeping unit 57c measures a gas supply duration (gas supply accumulative time) of carbon dioxide in which carbon dioxide gas has begun to be supplied. Then, the luminal cavity gas supply control unit 57 makes comparison between the resulting measured time and a preset time that has been preliminarily set.

More particularly, the power switch 51b is operated as shown by step S41 in FIG. 13. In response to such an operation, the luminal cavity gas supply control unit 57 outputs a gas supply signal to the valve unit 56. This allows the ECR 51 to enter the gas supply state. Under such a gas supply state, as shown by step S42, the timekeeping unit 57c begins to measure the gas supply duration elapsed after the gas supply signal has been outputted.

Next, the operation proceeds to step S43 and the luminal cavity gas supply control unit 57 makes comparison between the measured gas supply time, resulting from the timekeeping unit 57c, and the preset gas supply time, which is preliminarily set before starting the operation. Here, if the luminal cavity gas supply control unit 57 decides that the gas supply duration is less than the preset gas supply time, the operation is routed back to step S42 wherein the operation is executed to allow the ECR 51 to be sustained in the operative state, that is, gas supply is continuously performed. On the contrary, if the luminal cavity gas supply control unit 57 discriminates that the gas supply duration exceeds the preset gas supply time, the operation proceeds to step S44. In step S44, the luminal cavity gas supply control unit 57 interrupts outputting the gas supply signal to render the ECR 51.

Thus, by taking a structure configured to allow the gas supply duration, in which carbon dioxide gas can be supplied from the ECR to the endoscope, to be preliminarily set while enabling the gas supply duration, elapsed after the ECR has entered the gas supply state, to be measured by the timekeeping unit of the ECR, the luminal cavity gas supply control unit is able to make comparison between the preset gas supply time and the gas supply duration upon which the operative state of the ECR is controlled. This results in a capability for carbon dioxide gas to be prevented from being wastefully consumed from the gas container. Even with the presently filed embodiment, if the gas supply state is needed, the power switch 51b is operated again as shown in step S41 to render the ECR 51 operative. Additionally, the present gas supply time can be can be suitably set on, for instance, the centralized operation panel 9 and a preset value of the relevant gas supply time can be displayed on, for instance, the display panel.

Figure 14:
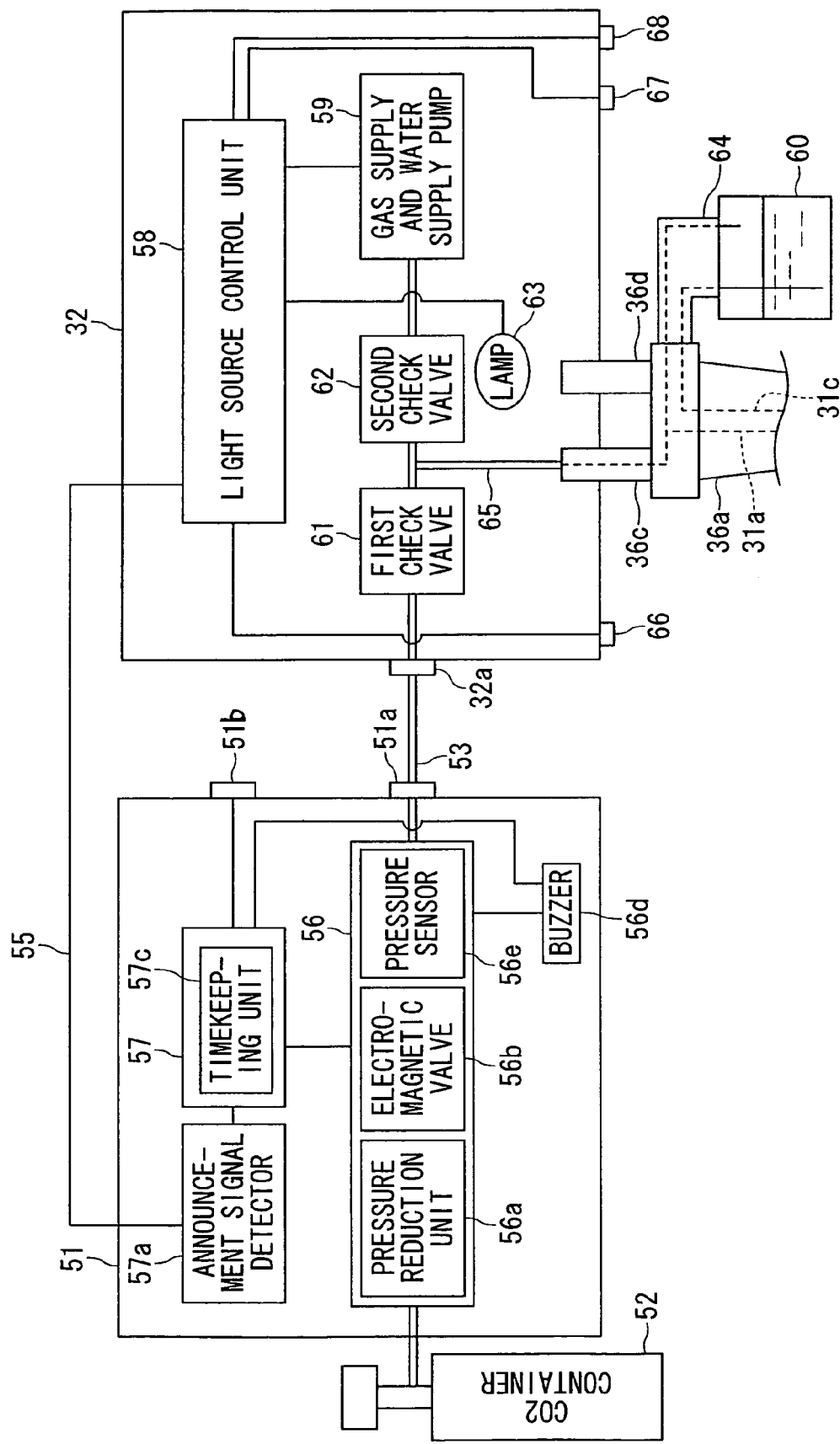
FIG. 14 is a block diagram for illustrating the relationship between an ECR and a second light source device of a modified form of the fifth embodiment according to the present invention.
Figure 15:
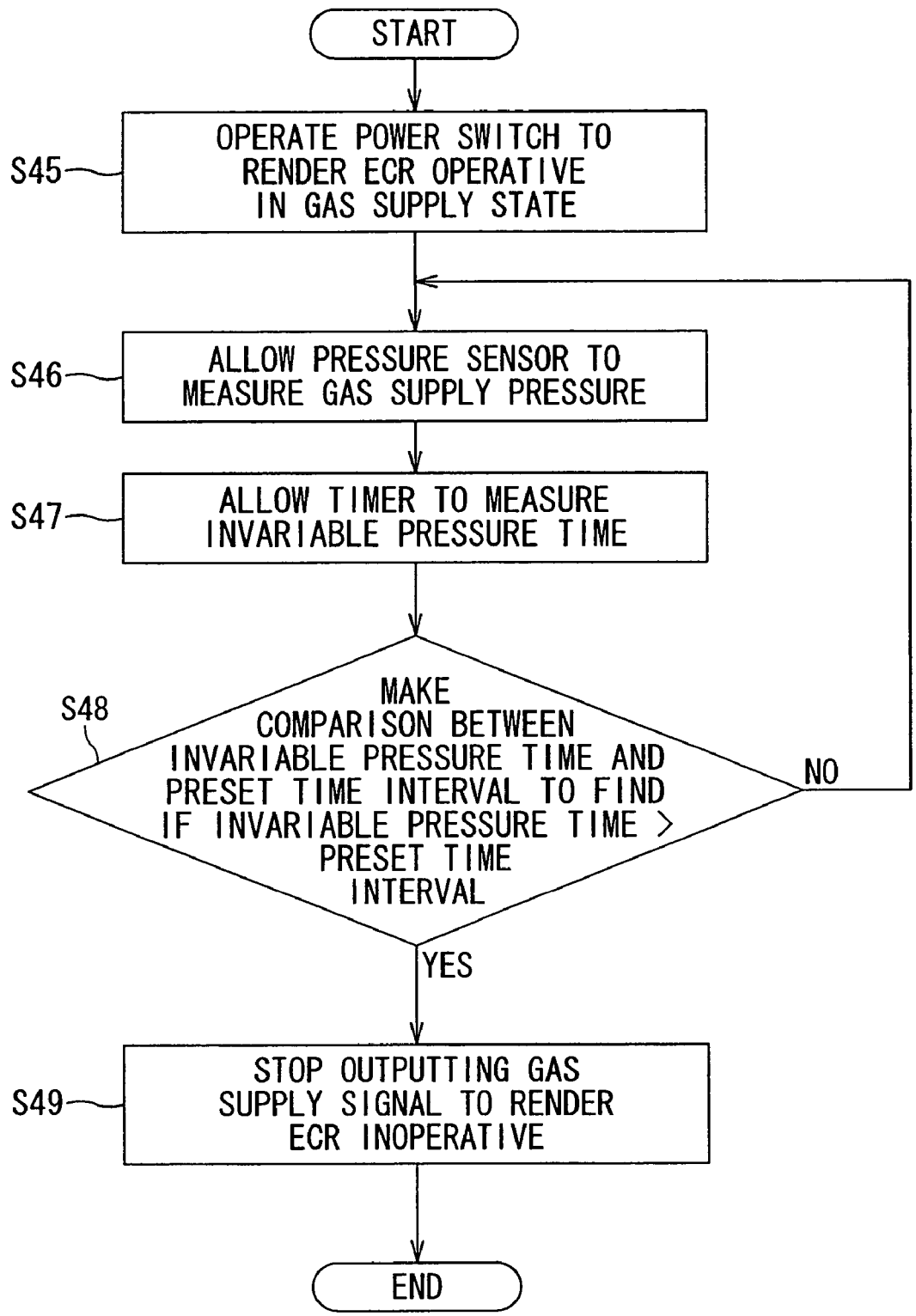
FIG. 15 is a flowchart illustrating exemplary control for switching the ECR, remaining under the gas supply state, to a gas supply stop state in another modified form.

A modified form is shown in FIGS. 14 and 15.

While with the presently filed embodiment set forth above, the timekeeping unit 57c is configured to detect the gas supply duration to allow the ECR 51 to shift from the operative state to the inoperative state, a modified form may be configured as shown in FIG. 14 such that the ECR 51 incorporates the timekeeping unit 57c and, in addition to this, a pressure sensor 56e, serving as a pressure measuring unit, which is replaced with the flow rate sensor 56c whereby upon execution of the operation to detect whether or not variation occurs in pressure for a fixed time interval, if no pressure varies within the fixed time interval, then, control is executed to switch the ECR 51 from the operative state to the inoperative state.

More particularly, the power switch 51b is operated as shown by step S45 in FIG. 15. In response to such operation, the luminal cavity gas supply control unit 57 outputs a gas supply signal to the valve unit 56. This allows the ECR 51 to enter the gas supply state. Then, the pressure sensor 56e measures a gas supply pressure as shown in step S46. Under such a gas supply state, subsequently, the timekeeping unit 57c of the luminal cavity gas supply control unit 57 enters a timekeeping state in association with the measuring operation of the pressure sensor 56e after which the operation is executed to measure an "invariable pressure duration" in which no variation takes place in a pressure value or in which a relevant variation falls in a predetermined minimal range.

Next, the operation proceeds to step S48. In step S48, the luminal cavity gas supply control unit 57 makes comparison between the invariable pressure duration and a preset time interval that is preliminarily set. In this moment, if the luminal cavity gas supply control unit 57 discriminates that the invariable pressure duration is less than the preset time interval, the operation is routed back to step S46 wherein the control is executed for the operative state to be sustained, that is, for the operation to be executed to continue the supply of gas. On the contrary, if the luminal cavity gas supply control unit 57 discriminates that the invariable pressure duration exceeds the preset time interval, the operation proceeds to step S49. In step S49, the luminal cavity gas supply control unit 57 interrupts outputting the gas supply signal, thereby performing control to switch the ECR 51 from the operative state to the inoperative state.

In such a way, with such a structure configured to allow the timekeeping unit of the ECR to measure a variation in the gas supply pressure of carbon dioxide gas, to be supplied from the ECR to the endoscope, in terms of time upon which the luminal cavity control unit makes comparison between the preset time interval and the invariable pressure duration after which the operation is executed to control the operative state of the ECR, it be comes possible to preclude carbon dioxide gas from being wastefully consumed from the gas container in a reliable fashion. Even with such a modified form, the gas supply state is needed, the power switch 51b is operated again rendering the ECR 51 operative. Further, an alternative may be such that the operation panel of the ECR is provided with a reset switch to provide means for resetting the invariable pressure duration to "0" when the reset switch is pressed down. Additionally, the predetermined time interval may be suitably set on, for instance, the centralized operation panel 9 and the relevant preset time interval may be displayed on, for instance, the display panel.

Figure 16:
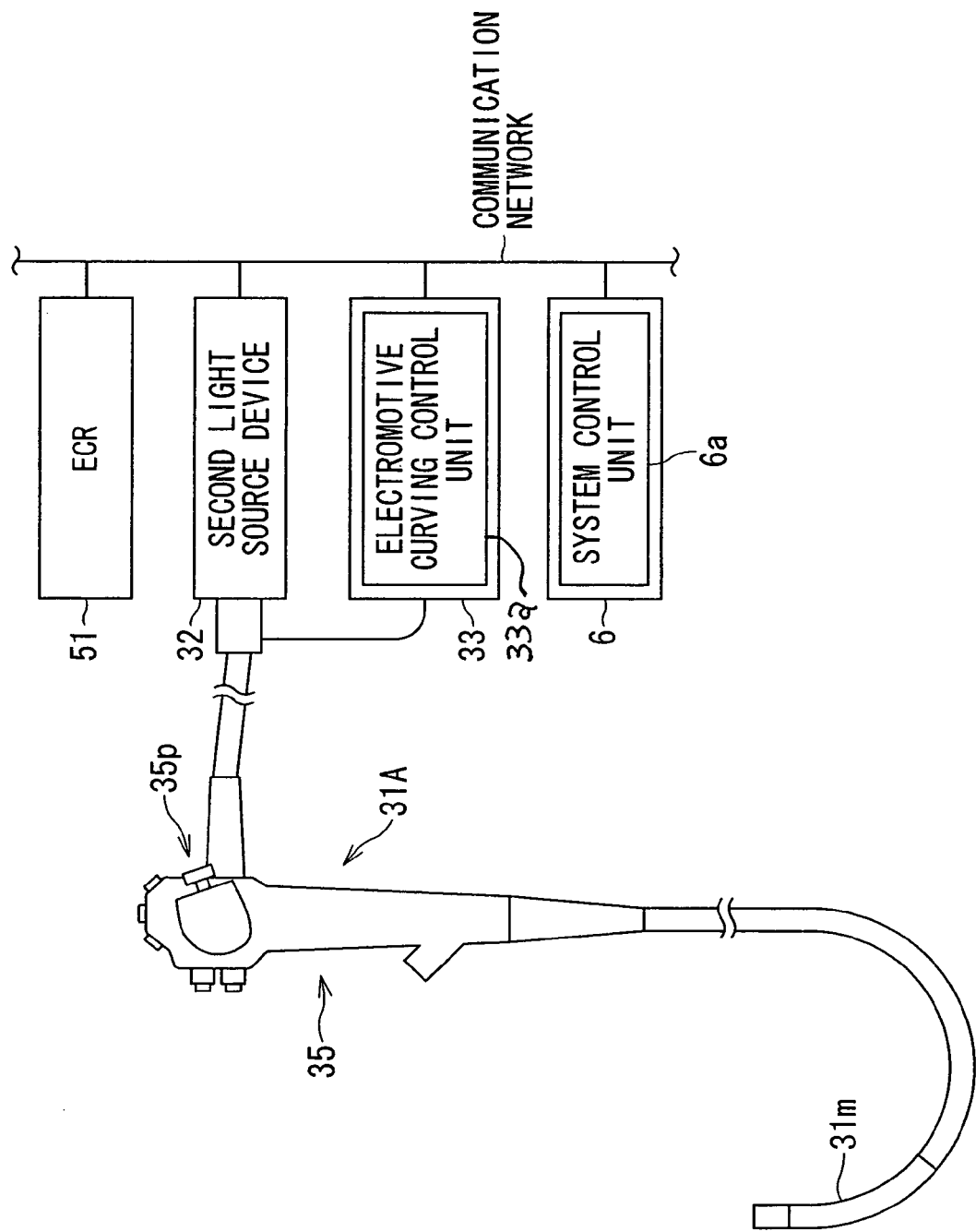
FIG. 16 is a view for illustrating an endoscopic system, with a manipulator equipped with a joystick, of another modified form of the fifth embodiment.

Another modified form is shown in FIG. 16.

Referring to FIG. 16, an endoscopic system having an endoscope, equipped with a joystick provided on the manipulator, is described. As shown in the drawing figure, in cases where an electromotive endoscope 31A is adopted, as a second endoscope, which is equipped with an operating lever 35p such as, for instance, a joystick, a control unit 6a of the system controller 6 may be enabled to execute luminal cavity gas supply control upon utilizing curvature data stored in an electromotive curving control unit 33a provided in the second CCU 33. That is, the control unit 6a may be configured to read out a curvature angle of a curving portion 31m of the inserter section of the endoscope 31A from such curving data upon which the ECR 51 is switched between the operative state and the inoperative state for thereby precluding wasteful consumption of carbon dioxide gas from the gas container.

More particularly, the control unit 6a of the system controller 6 is configured such that the control is executed for interrupting the gas supply under circumstances where there is curving data for the curving portion 31m to be extended straight or for the curving angle to be set to zero degree, or for interrupting the gas supply when no variation occurs in a value of curving data, related to the curving portion 31m, even after an elapse of a predetermined time interval.

Further, with an endoscope configured to curvedly move the curving portion upon pulling an associated curving wire, a rotary shaft of a curving operation knob, by which the curving wire is pulled for movements, may be provided with an encoder. With such an alternative, the system control unit 6a may be configured such that if the curving operation knob is operated and the encoder discriminates that a relevant rotational angle exceeds a preset value, the control unit 6a executes the operation to command starting the gas supply. This enables carbon dioxide gas to be reliably prevented from being wastefully consumed from the gas container before the endoscope begins to be used.

Sixth Embodiment

Figure 17:
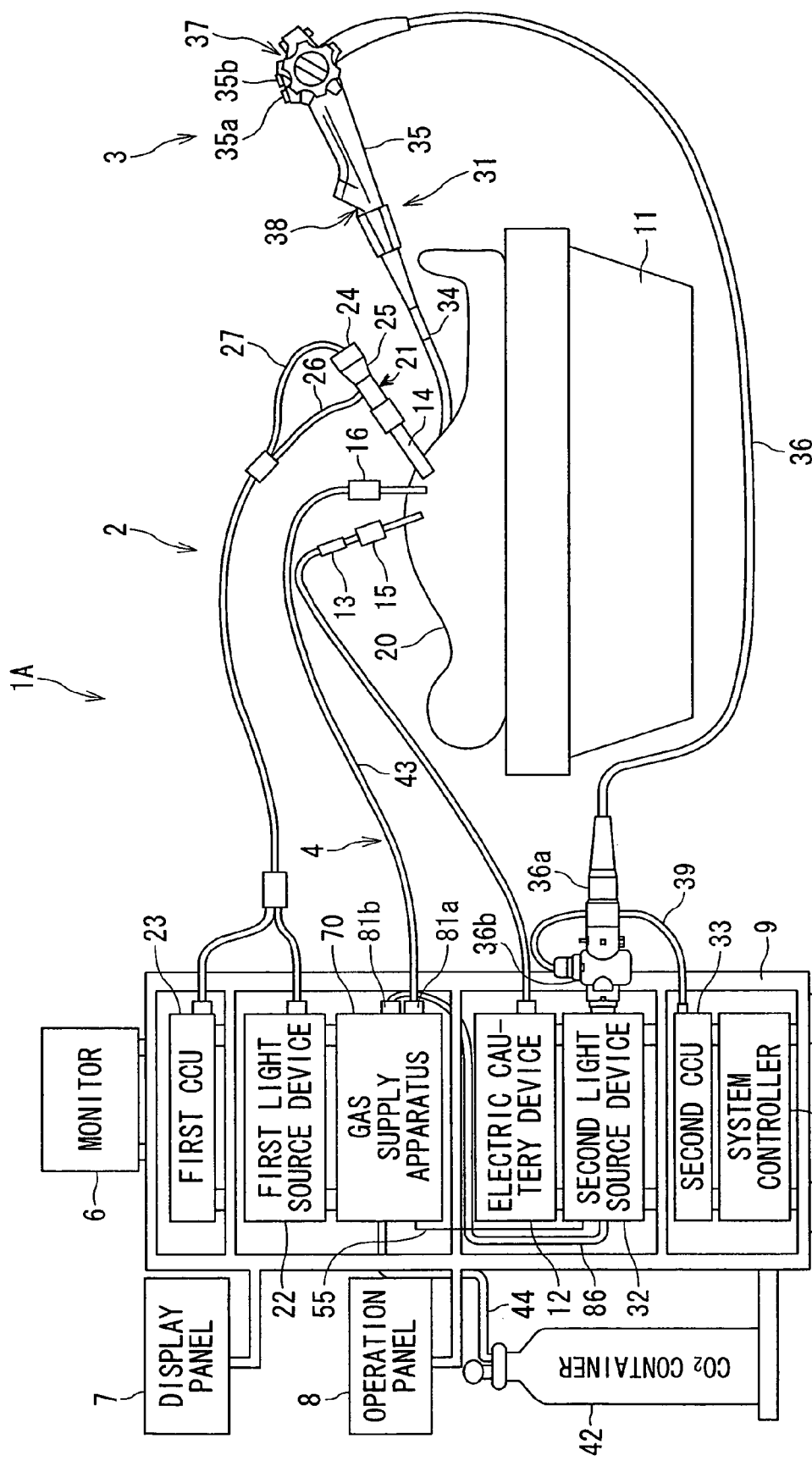
FIG. 17 is a view illustrating an endoscopic system, including a gas supply apparatus with functions of an abdominal insufflation device and an ECR, of a sixth embodiment according to the present invention.
Figure 20:
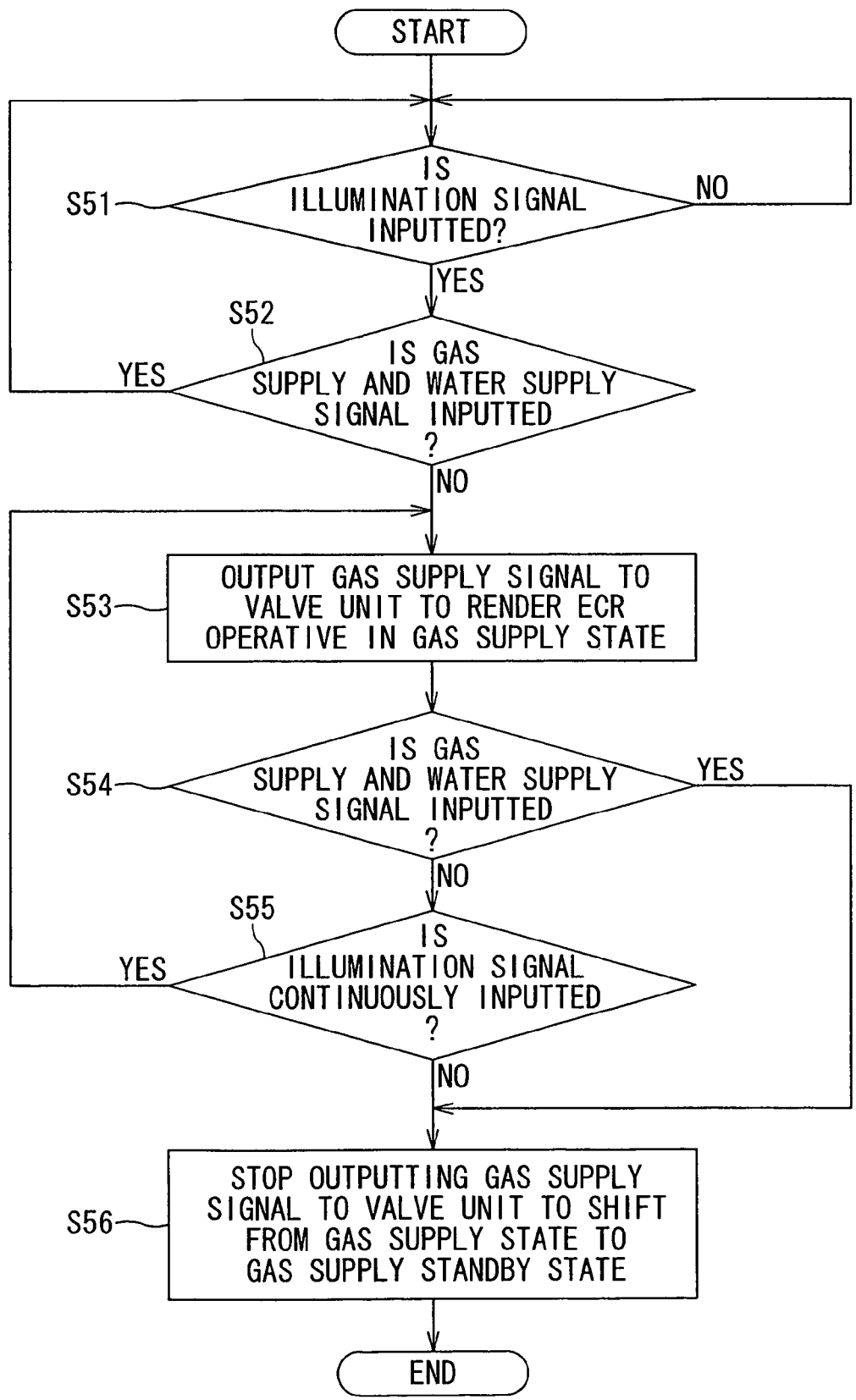
FIG. 20 is a flowchart for illustrating exemplary control of switching a luminal cavity flow path of the gas supply apparatus, remaining under a gas supply state, to a gas supply stop state.

Referring to FIGS. 17 and 20, an endoscopic system, equipped with a gas supply apparatus, of a sixth embodiment according to the present invention is described.

The present embodiment takes the form of a structure that incorporates, in place of incorporating the abdominal insufflation device 41 and first gas container 42 and the ECR 51 and second gas container 52, a gas supply apparatus 70, serving as a gas supply means, which has functions as the abdominal insufflation device 41 and the ECR 51, and a single gas container from which carbon dioxide gas is supplied to the gas supply apparatus 70 as shown in FIG. 17. Also, the first gas container 42 is used as the gas container in the presently filed embodiment. Moreover, the second light source device 32 and the gas supply apparatus 70 are connected to each other through the communication cable 55 to enable mutually related communications like the second light source device 32 and the ECR 51 that have been set forth above.

Figure 18:
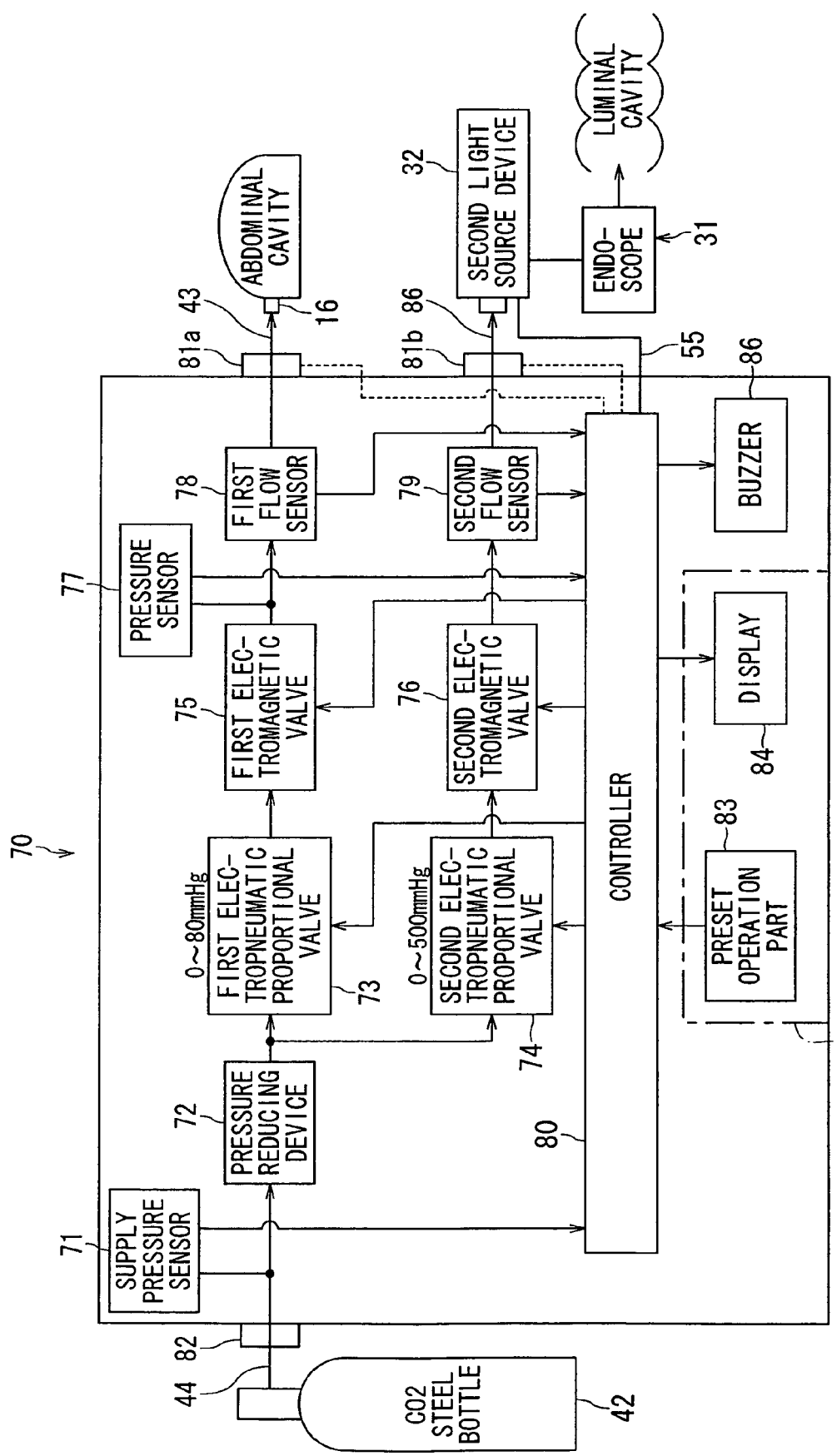
FIG. 18 is a view for illustrating a structure of a gas supply apparatus.

As shown in FIG. 18, the gas supply apparatus 70 is mainly comprised of a supply pressure sensor 71, a pressure reduction unit 72, first and second electropneumatic proportional valves 73, 74, a first electromagnetic valve 75, a second electromagnetic valve 76 that corresponds to the above-described electromagnetic valve 56b, a pressure sensor 77, a first flow rate sensor 78, a second flow rate sensor 79 that corresponds to the above-described flow rate sensor 56c, and a control unit 80. Further, the gas supply apparatus 70 includes, in addition to an abdominal cavity coupling 81a, which corresponds to the above-described abdominal cavity coupling 41a, and a luminal cavity coupling 81b, which corresponds to the above-described gas supply coupling 51a, a high-pressure fitting 82, a setting and operating section 83 and a display section 84. The setting and operating section 83 and the display section 84 are formed as a panel section 85. Also, reference numeral 86 designates a buzzer that corresponds to the buzzer 56d that has been discussed above.

The pressure reduction unit 72 has a downstream that is diverged into two flow paths. One the diverged flow paths includes an abdominal cavity flow path that is comprised of the first electropneumatic proportional valve 73, the first electromagnetic valve 75, the pressure sensor 77, the first flow rate sensor 78, the abdominal cavity coupling 81a, the abdominal cavity tube 43 and the third trocar 16. The other one of the diverged flow paths includes a luminal cavity flow path that is comprised of the second electropneumatic proportional valves 74, the second electromagnetic valve 76, the second flow rate sensor 79, the luminal cavity coupling 81b, a luminal cavity tube 86, the second light source device 32 and the endoscope 31.

The supply pressure sensor 71 measures a pressure of carbon dioxide gas evaporated and supplied from the first gas container 42 to output the measured result to the control unit 80. The pressure reduction unit 72 reduces the pressure of carbon dioxide gas, evaporated and supplied to the gas supply apparatus 70 via the high-pressure fitting 82, to a predetermined pressure.

The first electropneumatic proportional valve 73 operates to allow carbon dioxide gas, reduced in pressure by the pressure reduction unit 72, to be set to a gas supply pressure at a value ranging from approximately 0 to 80 mmHg depending on a control signal outputted from the control unit 80. In the meanwhile, the second electropneumatic proportional valve 74 operates to allow carbon dioxide gas, reduced in pressure by the pressure reduction unit 72, to be set to a gas supply pressure at a value ranging from approximately 0 to 500 mmHg depending on a control signal outputted from the control unit 80.

The first and second electromagnetic valves 75, 76 are opened or closed based on control signals outputted from the control unit 80. The pressure sensor 77 measures an abdominal cavity inside pressure to output the measured value to the control unit 80. The first and second flow rate sensors 78, 79 measure the flow rates of carbon dioxide gas to be supplied to the first and second couplings 81a, 81b, respectively, to output measured results to the control unit 80.

That is, carbon dioxide gas, stored in the first gas container 42 in a liquid form, is evaporated and delivered to the pressure reduction unit 72 by which carbon dioxide gas is reduced in pressure after which carbon dioxide gas is supplied to the abdominal cavity via the abdominal cavity flow path depending on the control signal outputted by the control unit 80 or supplied to the luminal cavity via the luminal cavity flow path depending on the control signal outputted from the control unit 80.

Figure 19:
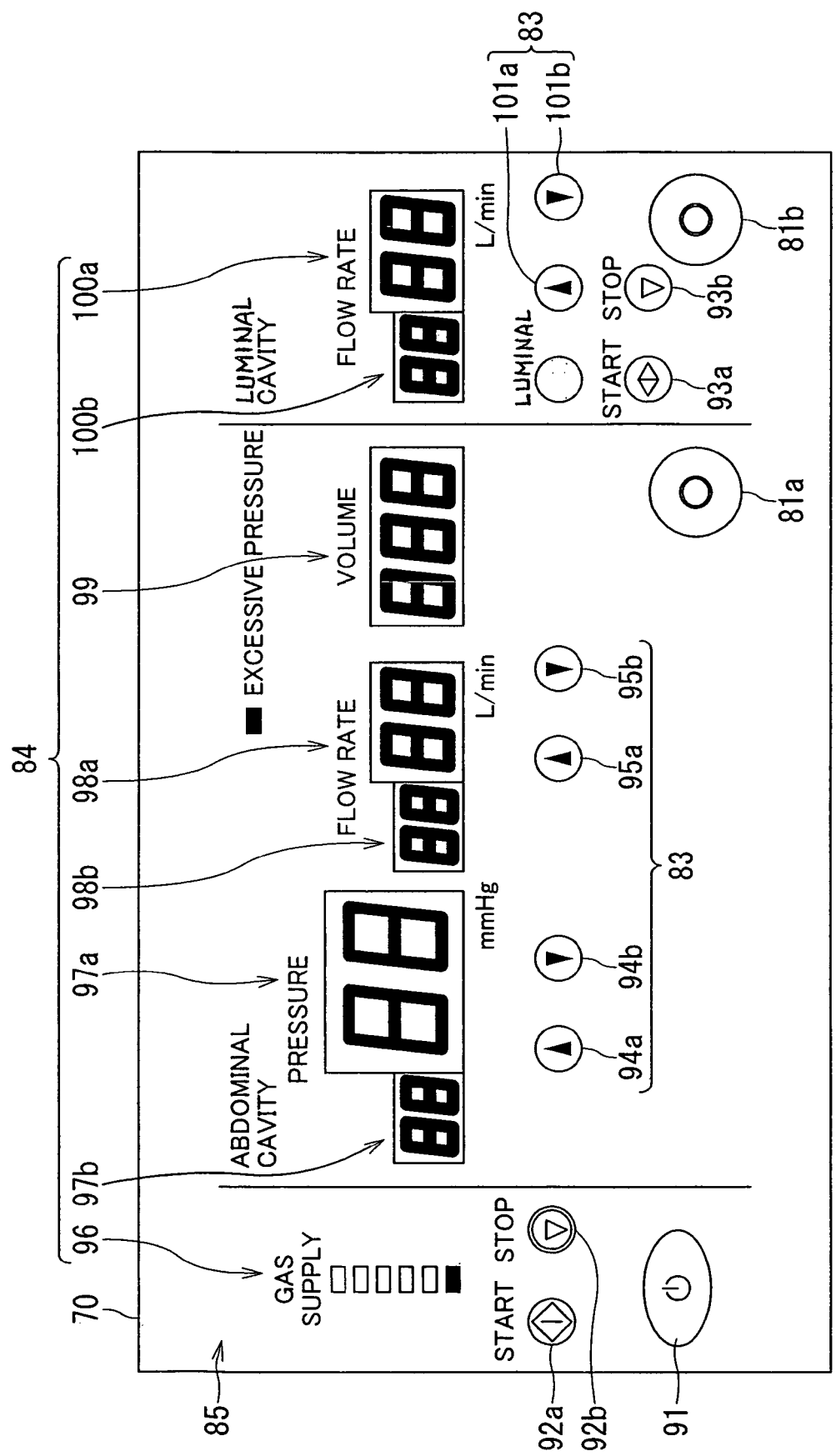
FIG. 19 is a view for illustrating a structure of a panel section of the gas supply apparatus.

As shown in FIG. 19, disposed on one face of the gas supply apparatus 70, on which the abdominal cavity coupling 81*a* and the luminal cavity coupling 81*b* are mounted, is a panel section 85 that includes a setting and operating section 83 and a display section 84.

Disposed on the panel section 85 are a power switch 91, an abdominal cavity gas supply start button 92*a*, a luminal cavity gas supply stop button 93*a*, an abdominal cavity gas supply stop button 92*b*, a luminal cavity gas supply stop button 93*b*, abdominal cavity pressure setting buttons 94*a*, 94*b* and abdominal cavity gas supply flow rate setting buttons 95*a*, 95*b*, both of which form part of the setting and operating section 83, luminal cavity gas supply flow rate setting buttons 101*a*, 101*b* which also form part of the setting and operating section 83, a residual gas volume indicator 96, abdominal cavity internal pressure indicators 97*a*, 97*b*, abdominal cavity flow rate indicators 98*a*, 98*b*, a supply gas total volume indicator 99, and luminal cavity flow rate indicators 100*a*, 10*b*. These indicators serve as the display section 84.

The power switch 91 serves as a switch by which a main power supply of the gas supply apparatus 70 is switched in an operative state or inoperative state. The abdominal cavity gas supply start button 92*a* serves as a button for commanding to start supplying carbon dioxide gas to the abdominal cavity. The abdominal cavity gas supply stop button 92*b* serves as a button for commanding to stop supplying carbon dioxide gas to the abdominal cavity. The luminal cavity gas supply start button 93*a* serves a button for commanding to start supplying carbon dioxide gas to the luminal cavity. The luminal cavity gas supply stop button 93*b* serves as a button for commanding to stop supplying carbon dioxide gas to the luminal cavity.

The abdominal cavity pressure setting button 94*a* and the gas supply flow rate setting buttons 95*a*, 101*a* are configured to vary relevant preset values in progressively increment directions upon press-down operations on the buttons. In the meanwhile, the abdominal cavity pressure setting button 94*b* and the gas supply flow rate setting buttons 95*b*, 101*b* are configured to vary preset values of associated parameters in progressively decrement directions upon press-down operations on the buttons.

The residual gas volume indicator 96 is arranged to provide a display of a residual volume of carbon dioxide gas remaining in the first gas container 42. The abdominal cavity internal pressure indicator 97*a* is arranged to provide a display of a measured result of the abdominal cavity internal pressure measured by the pressure sensor 77. In the meanwhile, the abdominal cavity internal pressure indicator 97*b* is arranged to provide a display of a preset pressure value preset upon press-down operations of, for instance, the abdominal cavity pressure setting buttons 94*a*, 94*b*.

The abdominal cavity flow rate indicator 98*a* is arranged to display a measured value resulting from the first flow rate sensor 78. The abdominal cavity flow rate indicator 98*b* is arranged to display a preset flow rate preset upon button operations executed on the abdominal cavity gas supply flow rate setting buttons 95*a*, 95*b*. The supply gas total volume indicator 99 is arranged to display a supply gas total volume acquired upon calculations executed in the CPU of the control unit 80 based on the measured value of the first flow rate sensor 78.

The luminal cavity flow rate indicator 100*a* is arranged to display a measured result resulting from the second flow rate sensor 79. In the meanwhile, the luminal cavity flow rate indicator 100*b* is arranged to display a preset flow rate preset by button operations of the luminal cavity gas supply flow rate setting buttons 101*a*, 101*b*.

Also, the abdominal cavity internal pressure and flow rates of gas to be supplied to the abdominal cavity and luminal cavity can be preset on the centralized operation panel 9 that has been set forth above. Further, the centralized display panel 8 may be provided with one value, preliminarily designated by an operator upon selecting one value or plural values from those displayed on the abdominal cavity internal pressure indicators 97*a*, 97*b*, the flow rate indicators 98*a*, 98*b*, 100*a*, 100*b*, and the supply gas total volume indicator 99.

Also, the second light source device and the other structures are the same as those of the first embodiment set forth above and the same component parts bear like reference numerals to omit redundant description. Further, with the second light source device, the illumination signal and the gas supply and water supply signal, outputted from the light source control unit 58, are inputted to the control unit 80 via the communication cable 55.

Now, description is made of a basic sequence of operations of the surgery operation system 1A with the gas supply apparatus 70 with the structure set forth above.

When using the gas supply apparatus 70, the abdominal cavity tube 43 is prepared and connected to the abdominal cavity coupling 81*a* and the third trocar 16. Also, if desired, the luminal cavity tube 86 is prepared and connected to the luminal cavity coupling 81*b* and the second light source device 32

Next, the power switch 91 is turned on. Then, this results in a condition under which the abdominal cavity internal pressure display indicator 97*a* of the panel section 85 displays a pressure value measured by the pressure sensor 77. Also, the abdominal cavity internal pressure indicator 97*b* and the flow rate display sections 98*b*, 100*b* are provided with displays of the abdominal cavity internal pressure and preset flow rates, respectively, which are preset on, for instance, the centralized operation panel 9.

Also, under circumstances where no abdominal cavity pressure or no flow rate are preset at this stage, operating the abdominal cavity internal pressure setting buttons 94*a*, 94*b* and the gas supply flow ratting buttons 95*a*, 95*b*, 101*a*, 101*b* allows the abdominal cavity pressure or flow rate to be preset.

Subsequently, the third trocar 16 is inserted to a predetermined position of a stomach portion in a predetermined stroke. The control unit 80 is inputted with, in addition to the measured result of the pressure sensor 71, a measured result resulting from the pressure sensor 77. This allows the residual gas volume of carbon dioxide gas in the first container 42 to be displayed on the residual gas indicator 96 and an abdominal cavity pressure value to be displayed on the abdominal cavity pressure indicator 77*a*. Here, when abdominal cavity insufflation needs to be achieved, the abdominal cavity gas supply start button 92*a* is operated. In response to such operation, the control unit 80 outputs a gas supply signal to the first electromagnetic valve 75, which is consequently rendered operative in the open state to establish an "abdominal-cavity carbon gas supply state" under which carbon dioxide gas is supplied to the abdominal cavity via the abdominal cavity flow path.

In the meanwhile, when supplying gas to a luminal cavity, first, the inserter section 34 of the endoscope 31 is inserted to a predetermined site inside a large intestine from, for instance, an anus after which the luminal cavity gas supply start button 93*a* is operated. This allows carbon dioxide gas to reach the gas supply and water supply button 35*a* of the endoscope 31 via the luminal cavity flow path and the gas supply apparatus 70 enters a "gas supply standby state" under which carbon dioxide gas is available to be supplied upon operation of the associated button.

More particularly, the gas supply apparatus 70, equipped in the surgery operation system 1A of the presently filed embodiment, executes the operation to confirm whether or not an illumination signal, outputted from the light source control unit 58 provided in the second light source device 32, is inputted to the control unit 80 as shown by step S51 in FIG. 20. Here, if the control unit 80 does not confirm that the illumination signal is inputted, the gas supply apparatus 70 enters the "gas supply standby state".

In the meanwhile, if in step 51 in FIG. 20, it is confirmed that the illumination signal is inputted, the control unit 80 allows the operation to proceed to step S52. In step S52, the control unit 80 confirms whether or not the control unit 80 is applied with the gas supply and water supply signal from the light source control unit 58. In step S52, the control unit 80 confirms whether or not the gas supply ad water supply signal is inputted from the light source control unit 58 that has been mentioned above. Here, if the control unit 80 confirms that the gas supply and water supply signal is inputted, then, the gas supply apparatus 70 enters the "gas supply state".

On the contrary, if the control unit 80 does not confirm that the gas supply and water supply signal is inputted, the operation proceeds to step S53. In step S53, the control unit 80 outputs the gas supply signal to the second electromagnetic valve 76. This allows the second electromagnetic valve 76 to be rendered operative to shift from the closed state to the open state, resulting in the gas supply state to supply carbon dioxide gas from the second gas container to the second light source device 32 via the luminal cavity low path. When this takes place, the buzzer 56d is activated to intermittently generate the electronic sounds. Also, a gas leakage status is established, as shown in FIG. 4, under which supplied carbon dioxide gas belches from the bore portion 35d of the gas supply and water supply button 35a.

As shown in FIG. 5 already described above, upon operation of an operator with his finger to block the bore portion 35d of the gas supply and water supply button 35a, carbon dioxide gas, leaking from the bore portion 35d, is supplied to the downstream gas supply conduit 31b via the bent pipe 35e. This results in the "luminal-cavity carbon dioxide gas supply state" under which carbon dioxide gas is supplied to the luminal cavity via the nozzle mentioned above.

If the gas supply state is established as shown in step S53, the control unit 80 confirms as shown in step S54 whether or not the gas supply and water supply signal is inputted from the light source control unit 58. In this moment, if the control unit 80 does not confirm that the gas supply and water supply signal is inputted, the operation proceeds to step S55. In step S55, the control unit 80 confirms whether or not the illumination signal is continuously inputted. In this moment, if the control unit 80 confirms that the illumination signal is inputted, the operation proceeds to step S53 in which the gas supply state is sustained.

By contrast, if the control unit 80 confirms in step S54 that the gas supply and water supply signal is inputted or if the control unit 80 can not confirm in step S55 that the illumination signal is inputted, the operation proceeds to step S56.

In step S56, the control unit 80 interrupts outputting the gas supply signal to the second electromagnetic valve 76. In response to such an operation, the valve is switched from the open state to the closed state. This interrupts supplying carbon dioxide gas from the second gas container 52 to the second light source device 32 via the ECR 51 and, thereafter, the buzzer 56d is deactivated to stop generating sounds.

In such a way, the presently filed embodiment takes the form of a structure wherein under circumstances where the second light source device and the gas supply apparatus are connected to each other via the communication cable and the illumination lamp, provided in the second light source device, is lighted up, the light source device control unit of the second light source device outputs the illumination signal and gas supply and water supply signal to the control unit of the gas supply apparatus. With such a structure, the control unit of the gas supply apparatus confirms the presence of or absence of the illumination signal and gas supply and water supply signal after which the second electromagnetic valve, provided in the luminal cavity flow path of the gas supply apparatus, is controlled to enable switching between the gas supply state and the gas supply interruptive state.

By so doing, while the ECR 51 enters the gas supply state under circumstances where the illumination signal is outputted from the second endoscope to the control unit of the gas supply apparatus after the luminal cavity gas supply start button is operated to be switched into a condition wherein gas is supplied via the luminal cavity flow path, the ECR remains in the gas supply interruptive state under a condition where the outputting of the illumination signal is interrupted or under a condition where the gas supply and water supply signal is outputted. Accordingly, upon manipulation of a medical staff to operate the light source switch or the lamp switch of the second light source device for turning off the light source lamp, the ECR 51 enters the gas supply interruptive state under which gas supply through the luminal cavity flow path of the gas supply apparatus is interrupted in association with the turnoff operation of the light source lamp. This results in a capability of reliably addressing issues resulting from wasteful consumption of carbon dioxide gas from the second gas container, connected to the gas supply apparatus via the luminal cavity flow path, when no endoscopic observation is performed. Other operations and advantageous effects are similar to those of the embodiment set forth above.

An alternative may also be structured such that the gas supply apparatus 70 is connected to the system controller 6 through a communication line, which is not shown, to control the surgery operation system 1 as a whole in a lump sum.

Another alternative may be configured such that in place of permitting the control unit 80 to controllably switch the luminal cavity flow path between the gas supply state and the gas supply interruptive state depending on the illumination signal and the gas supply and water supply signal outputted from the light source control unit of the second light source device, such switching control may be executed by means of the system controller 6, as shown in the flow chart of FIG. 8 that has been discussed above, upon confirming whether or not the second light source device and the second CCU 33 lie in the respective operative states.

As shown in the third embodiment described above, an alternative may include the light source connector detection sensor 69 for detecting whether or not there is a status wherein the light source connector 35d is connected to the second light source device 32 upon which if the light source connector 36d is pulled out of the second light source device 32 under circumstances where the gas supply is carried out via the luminal cavity flow path, the control unit 80 executes the operation for controllably interrupting the gas supply via the luminal cavity flow path.

Further, as already described above with reference to the fourth embodiment, another alternative may be such that the CPU of the control unit 80 obtains a supply gas total volume upon executing the calculation based on the measured value of the second flow rate sensor 79 upon which, as shown in FIG. 11 discussed above, the control unit 80 executes comparison between the preset amount and the supply gas total volume for thereby controlling the gas supply state via the luminal cavity flow path.

Further, as already described above with reference to the fifth embodiment, still another alternative may be such that the gas supply apparatus 70 is provided with the timekeeping unit 57c, which counts time during which the second electromagnetic valve 76 remains in the open state, for measuring the gas supply duration upon which, as shown in FIG. 13 mentioned above, the control unit 80 makes comparison between the preset gas supply time and the gas supply duration to control the gas supply state via the luminal cavity flow path.

Although the embodiment has been described above with reference to an exemplary structure wherein under a condition where the flow rate sensor 56c detects the occurrence of carbon dioxide gas being supplied from the ECR 51 or under a condition where the second flow rate sensor 79 detects the occurrence of carbon dioxide gas being supplied via the luminal cavity flow path of the gas supply apparatus 70, the buzzers 56d, 86 are activated in sound generating states to allow an operator or the like to recognize a condition under which carbon dioxide gas is available to be supplied to the luminal cavity via the endoscope 31, not only the sound generation but also a structure, described below, may allow the operator or the like to be notified with information indicative of a condition under which carbon dioxide gas is supplied to the luminal cavity via the endoscope 31.

Figure 21:
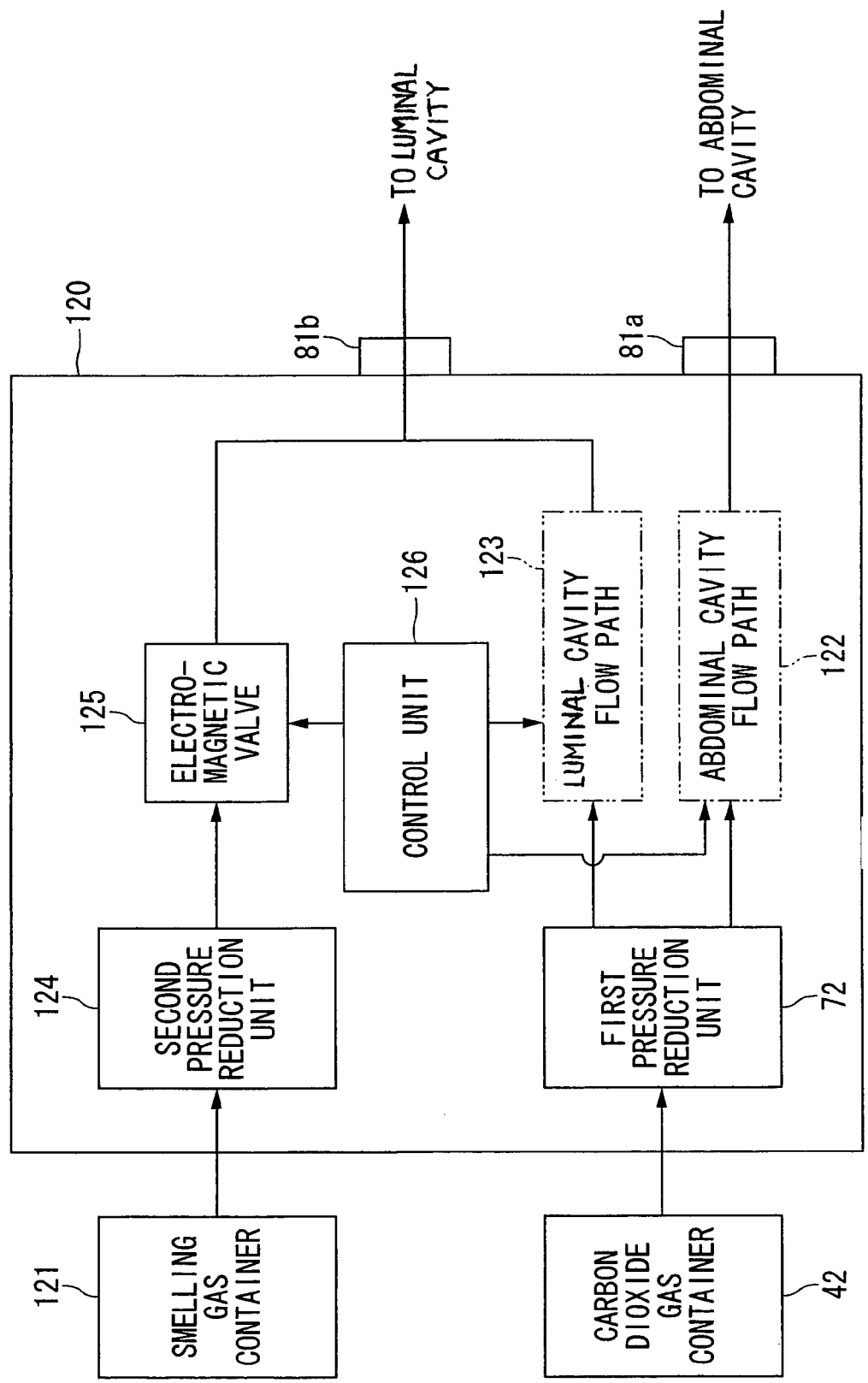
FIG. 21 is a view illustrating an endoscopic system, including a smelling gas container, of a modified form of the sixth embodiment.

One modified form is shown in FIG. 21.

For the modified form shown in the drawing figure, an endoscopic system having a smell-applying container. As shown in FIG. 21, prepared in addition to the carbon dioxide gas container 42 for a gas supply apparatus 120 is a smell-applying container 121 for applying carbon dioxide gas with a smell. The gas supply apparatus 120 has a structure that includes, in addition to the abdominal cavity flow path 122 and the luminal cavity flow path 123, which have been described above with reference to the gas supply apparatus 70 shown in FIG. 18 mentioned above, a second pressure reduction unit 124, by which gas in the smell-applying container 121 is preset to a predetermined pressure, and an electromagnetic valve 125 that controls whether to render smelled gas to be available under a gas supply state. Reference numeral 126 designates a control unit that controls an abdominal cavity flow path 122, a luminal cavity flow path 123 and an electromagnetic valve 125. Other structures are similar to those of the sixth embodiment set forth above.

When supplying gas to the luminal cavity via the luminal cavity flow path 124, the control unit 126 outputs a control signal to the electromagnetic valve 125. Then, the electromagnetic valve 125 is rendered operative in an open state and carbon dioxide gas, supplied to the luminal cavity, is admixed with smell gas.

By so doing, under circumstances where carbon dioxide gas is supplied, the presence of carbon dioxide gas belching from the bore portion 35d of the gas supply and water supply button 35a, provided in the manipulator 35 of the endoscope 31, is filled with a smell (i.e., recognizable odor or smelly gas) in, for instance, an operation room, whereby the operator recognizes the presence of carbon dioxide gas being supplied.

Figure 22:
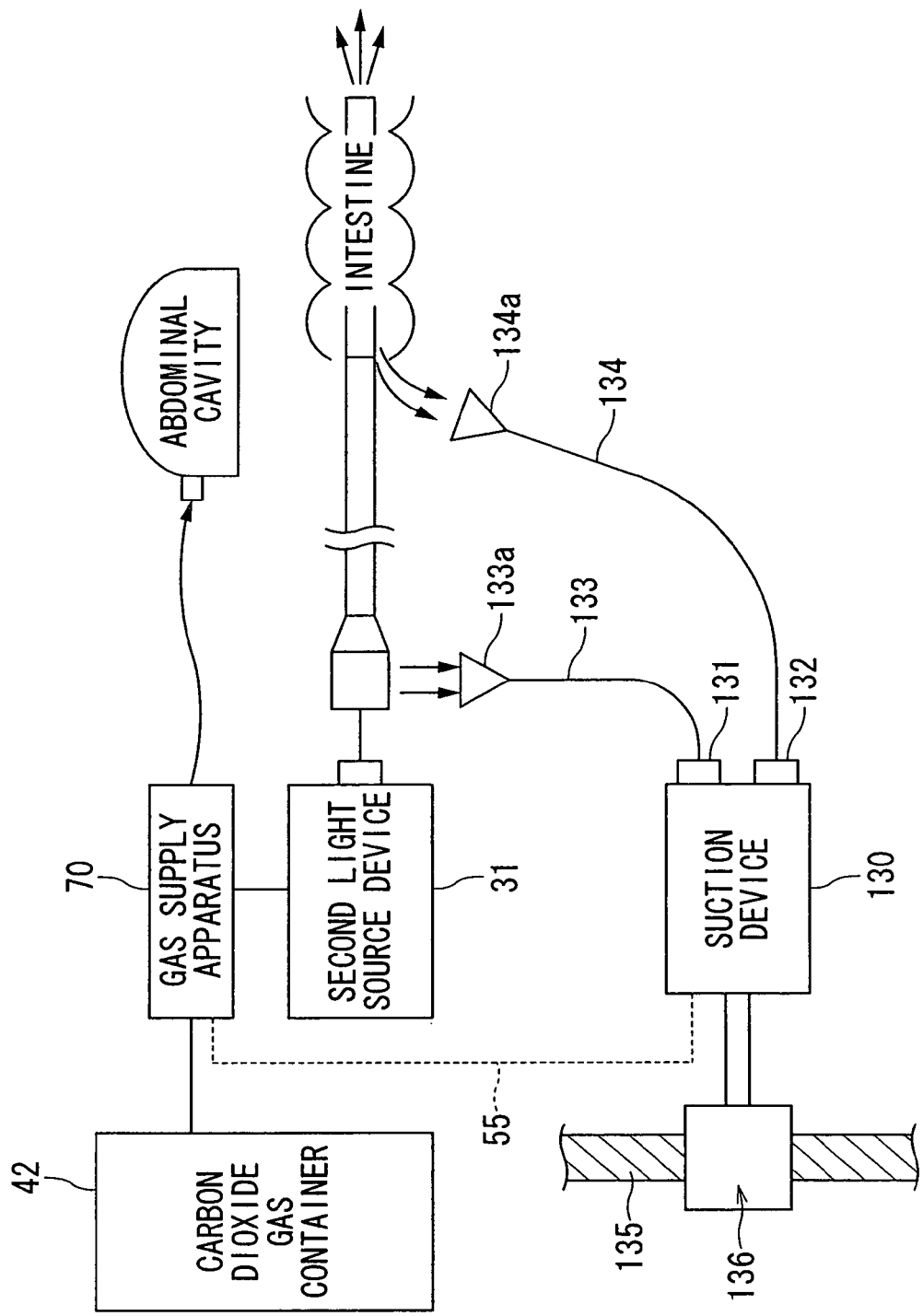
FIG. 22 is a view illustrating an endoscopic system, including a suction device, of another modified form of the sixth embodiment.

Another modified form is shown in FIG. 22.

Another modified form, shown in the drawing figure, relates to an endoscopic system having a suction device. As shown in the drawing figure, in addition to the gas supply apparatus 70, the operation room may be provided with the suction device 130 for collecting carbon dioxide gas belching from the gas supply and water supply button or carbon dioxide gas leaked from, for instance, an anus of a patient.

The suction device 130, of the presently filed modified form, is provided with a suction pump that is not shown. The suction device 130 includes a plurality of suction ports 131, 132. Extending from the suction ports 131, 132 are, for instance, suction conduits 133, 134 which have distal ends provided with sucking portions 133a, 134a, respectively. In addition, the suction device 130 takes a structure that exhausts carbon dioxide gas drawn from a ventilation opening 136 mounted on a wall 135 of the operation room.

For the purpose of appropriately locating the sucking portions 133a, 134a in desired places, a sucking portion support device, which is not shown, may be provided. The sucking portion support device may be directly mounted to a ceiling or wall of the operation room or may be formed in a support stand.

With an operation room provided with the suction device in such a way, it becomes possible to prevent the operation room from being pervaded with carbon dioxide gas during supply of carbon dioxide gas.

Also, the gas supply apparatus 70 and the suction device 130 may be connected to each other through, for instance, the communication cable 55 that is shown by a broken line. With such a connection, it may be possible to operate the suction device 130 in conjunction with a phase in which the gas supply is effectuated by the gas supply device 70 to the luminal cavity, thereby enabling for carbon dioxide gas to be efficiently drawn.

Seventh Embodiment

Figure 23:
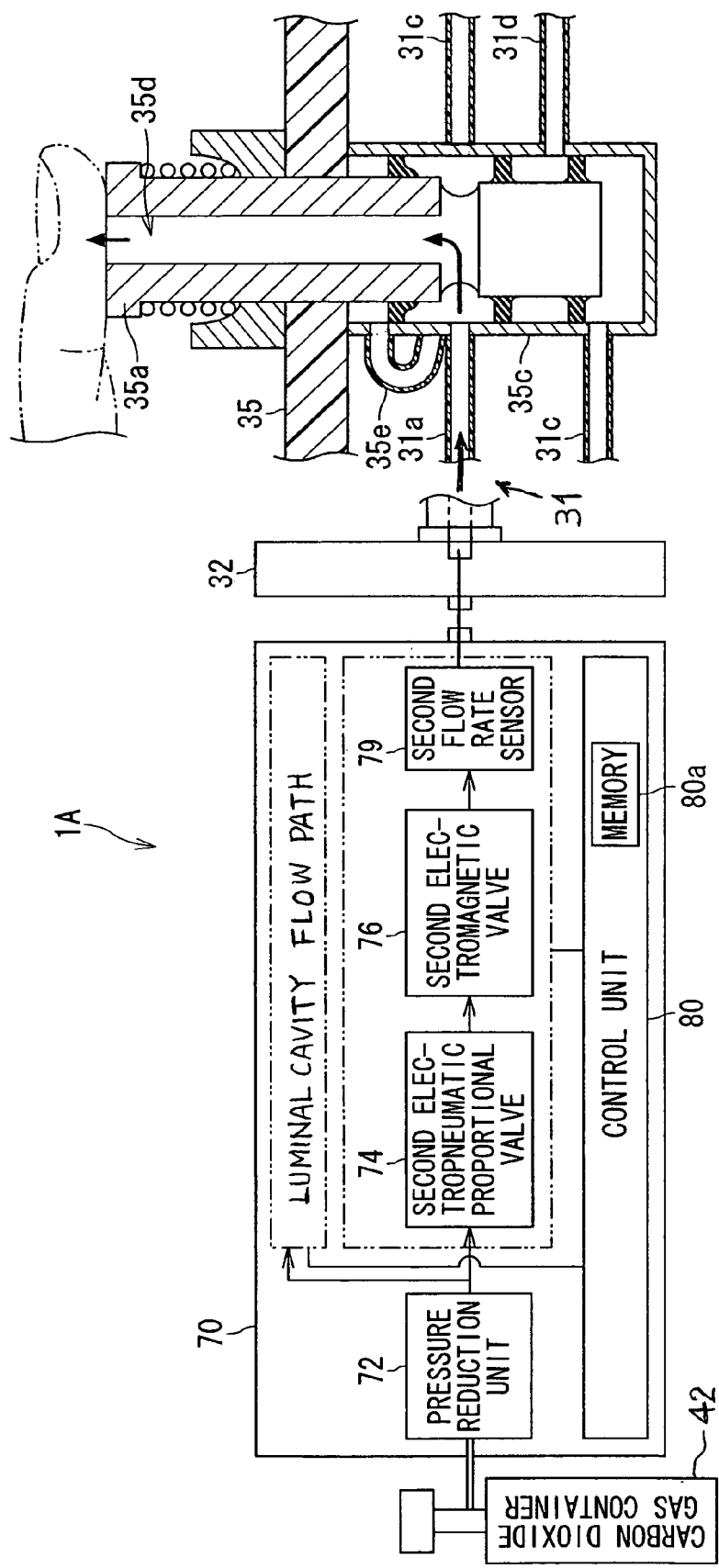
FIG. 23 is a view for illustrating the relationship between a gas supply apparatus and a gas supply and water supply switch of an endoscope, of an endoscopic system of a seventh embodiment according to the present invention.
Figure 24:
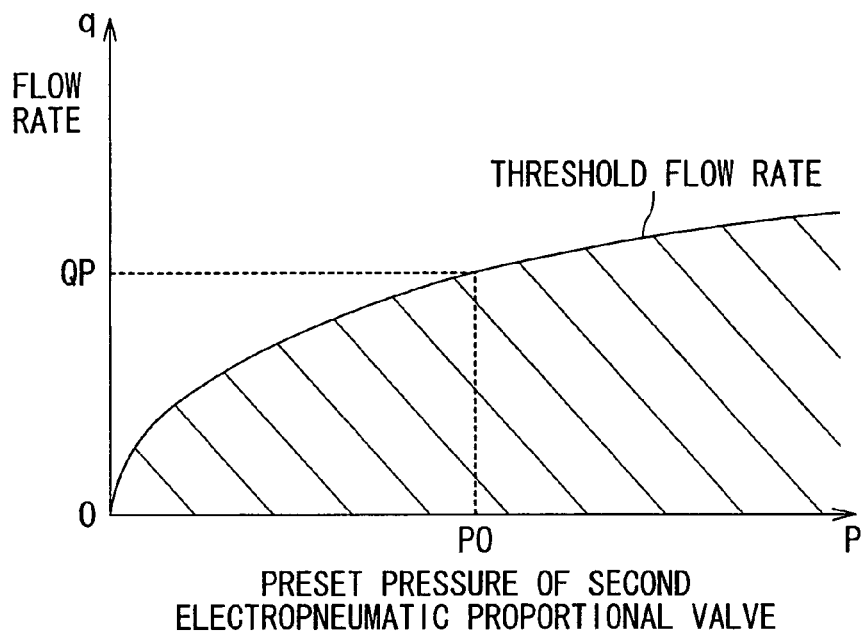
FIG. 24 is a view for illustrating a threshold value used in setting a gas supply flow rate.
Figure 25:
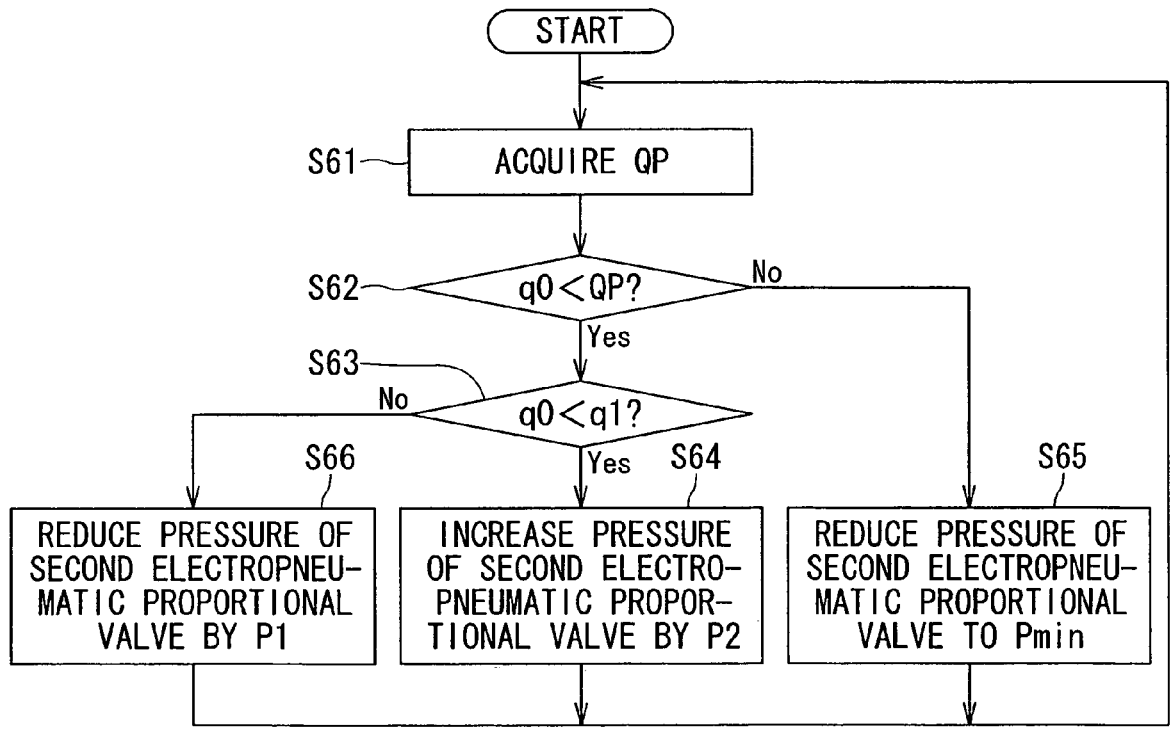
FIG. 25 is a flowchart for illustrating control for the flow rate of gas passing through a luminal cavity flow path provided in the gas supply apparatus.
Figure 26:
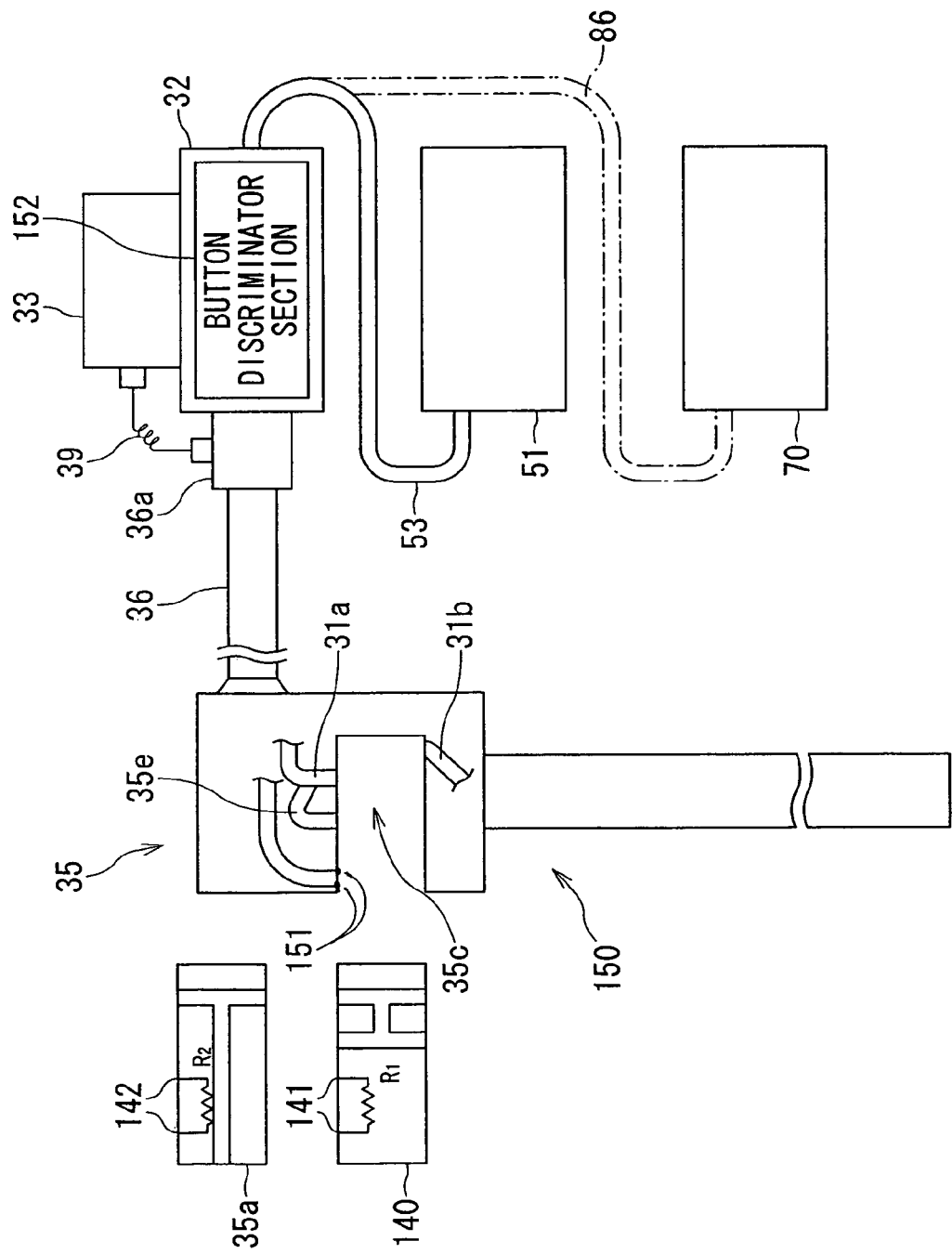
FIG. 26 is a view for illustrating a structural example of an endoscopic system, in which buttons are provided with resistances for a gas supply and water supply button and a carbon dioxide gas button provided in a gas supply and water supply cylinder, of an endoscopic system of an eighth embodiment according to the present invention.

Referring to FIGS. 23 to 25, an endoscopic system, equipped with a gas supply apparatus, of a seventh embodiment according to the present invention is described.

The gas supply apparatus of the present embodiment takes the form of a structure in which as shown in FIG. 23, the amount of belching carbon dioxide gas leaked from the bore portion 35d of the gas supply and water supply 35a is reduced for thereby suppressing the occurrence of wasteful consumption of carbon dioxide gas from the second container 24.

With the presently filed embodiment, attention is focused on a structure as shown in FIG. 23 wherein under circumstances where carbon dioxide gas is supplied to the endoscope 31 via the luminal cavity flow path of the gas supply apparatus 70, the flow rate of carbon dioxide gas can be varied by changing a diameter of a flow path for carbon dioxide gas to flow upon selecting one of a status wherein the bore portion 35d, formed in the gas supply and water supply button 35a provided in the manipulator 35 of the endoscope 31, is unblocked by a finger as indicated by a phantom line and another status wherein the bore portion 35d is blocked with the finger.

More particularly, under a condition wherein the bore portion 35d of the gas supply and water supply button 35a is blocked, the gas supply flow rate is set by the control unit 80 based on the relationship between a gas supply pressure of the electropneumatic proportional valve 74, under a status where carbon dioxide gas is supplied to the downstream gas supply conduit 31b, and the flow rate resulting from the second flow rate sensor 79.

When it is supposed that the gas supply pressure of the electropneumatic proportional valve 74 lies at P as shown in FIG. 24 under circumstances where the bore portion 35d of the gas supply and water supply button 35a is blocked, the flow rate Q varies in a manner indicated by a curve as shown in FIG. 24. The flow rate Q is referred to as a threshold flow rate.

For instance, if the luminal cavity internal pressure is high when supplying carbon dioxide gas to the luminal cavity under circumstances where the bore portion 35*d* of the gas supply and water supply button 35*a* is blocked, the gas supply flow rate Q1 for the luminal cavity is expressed as Q1<Q and lies in a range indicated by a hatched area. On the contrary, under circumstances where the bore portion 35*d* of the gas supply and water supply button 35*a* is left in an open state, the belching flow rate Q2 has a relationship expressed as Q2>Q and lies in a range indicated by a non-hatched (blank) area in the drawing figure.

That is, the non-hatched area in FIG. 24 represents a status under which the bore portion 35*d* is opened and, in contrast, the hatched area represents another status wherein the bore portion 35*d* is blocked. Therefore, the control unit 80 is configured in a structure wherein a gas supply state is discriminated upon comparison between a measured value (indicated as "q") resulting from the second flow rate sensor 79 and the threshold value Q after which the second electropneumatic proportional valve 74 is regulated. Also, the relationship between the gas supply pressure P0 and the threshold flow rate Q is preliminarily stored in the memory 80*a*, serving as a button discriminating means, which is provided in the control unit 80.

More particularly, with the gas supply apparatus 70 equipped in the surgery operation system 1 of the presently filed embodiment, if a luminal cavity gas supply start button, which is now shown, is operated, the control unit 80 acquires the threshold flow rate QP associated with the gas supply pressure P0 of the second electropneumatic proportional valve 74 as shown by step S61 in FIG. 25. Further, upon receipt of the flow rate q0, which is the measured value, of the second flow rate sensor 79, after which the operation proceeds to step S62.

In step S62, the control unit 80 makes comparison between the flow rate q0, acquired from the second flow rate sensor 79, and the threshold flow rate Q0. In particular, confirmation is made whether or not there is the relationship expressed as q0<QP.

In the present moment, if discrimination is made that the flow rate q0 is greater than the threshold flow rate Q0, then, it is discriminated that the bore portion 35*d* of the gas supply and water supply button 35*a* remains in the open state, and the operation proceeds to step S65. In step S65, the control unit 80 executes control such that the gas supply pressure of the second electropneumatic proportional valve 74 is lowered to an adequately small pressure of Pmin in the order of, for instance, 30 mmHg. Thereafter, the operation proceeds to step S61, in which the flow rate q0 is acquired again. With such operations, the control unit 80 executes control so as to minimize the flow rate of carbon dioxide gas belching from the bore portion 35*d* under the condition where the bore portion 35*d* is blocked.

On the contrary, if it is discriminated in step S62 that the relationship, expressed as q<Q, is not established, then, it is discriminated that the bore portion 35*d* of the gas supply and water supply button 35*a* remains in a blocked state, and the operation proceeds to step S63. In step S63, the control unit 80 makes comparison between a gas supply target flow rate q1 and the flow rate q0 for gas to be supplied to the luminal cavity. More particularly, confirmation is made whether or not the relationship expressed as q0<q1 is established. In this moment, if the control unit 80 discriminates that the flow rate q0 is less than the target gas flow rate q1, the operation proceeds to step S64. In step S64, the control unit 80 executes control in such a way as to raise the gas supply pressure of the second electropneumatic proportional valve 74 by a predetermined amount of a value (+p2). Subsequently, under the condition where the bore portion 35*d* is blocked, the control unit 80 is able to supply gas to the inside of the luminal cavity under a desired gas supply condition under which the flow rate is close to the target gas flow rate.

In contrast, if discrimination is made in step S63 that the flow rate q0 is greater than the target gas flow rate q1, the operation proceeds to step S66. In step S66, the control unit 80 executes control in such a way as to lower the gas supply pressure of the second electropneumatic proportional valve 74 by a predetermined amount of a value (−p1). Subsequently, the operation proceeds to step S61, in which the flow rate q0 is acquired again.

Then, the control unit 80 repeatedly executes the operations for control mentioned above during a period in which the luminal cavity gas supply start button 93*a* is operated to allow gas to be supplied through the luminal cavity flow path.

Due to an ability of the control unit wherein during a period in which gas is supplied through the luminal cavity flow path, provided in the gas supply apparatus and including the second electropneumatic proportional valve and the second flow rate sensor, the control unit makes comparison between the flow rate and the threshold flow rate and between the flow rate and the target gas supply flow rate for thereby regulating the gas supply pressure of the second electropneumatic proportional valve, gas can be supplied to the luminal cavity at the target flow rate whereas when the operator needs no gas supply, that is, under a condition where the bore portion of the gas supply and water supply button is unblocked, wasteful consumption of carbon dioxide gas can be reliably suppressed.

Eighth Embodiment

Referring to FIGS. 26 to 30, an endoscopic system, equipped with a gas supply apparatus, of an eighth embodiment according to the present invention is described.

Under circumstances where the gas supply and water supply button 35*a* is provided in the gas supply and water supply cylinder 35*c*, provided in the manipulator 35 as shown in FIG. 4 that has been mentioned above, carbon dioxide gas belches from the bore portion 35*d* formed in the gas supply and water supply button 35*a*. It is conceived that in order to address such a defect, the gas supply and water supply button 35*a* is replaced with a carbon dioxide gas supply button (hereinafter merely abbreviated as carbon dioxide gas button) with which the bore portion 35*d* is dispensed.

However, there is a need for the gas supply and water supply button 35*a* and the carbon dioxide gas button to be creatively used for the single gas supply and water supply cylinder 35*c* in consideration of a busy condition, whereby some detects my occur if a switch is erroneously mounted to be different from that of an intended use.

With the present embodiment, in order to address such defect, the gas supply and water supply button 35*a* and the carbon dioxide gas button are provided with resisters with different resistance values R1 and R2, respectively, which serve as switch detectors.

Further, the manipulator 35 of the endoscope 31 is provided with a contact site with which electrical contacts 141, 142, provided on the buttons 35*a*, 140, respectively, are electrically connected.

In addition, the second light source device 32, to which the endoscope 150 is connected, is provided with a button discriminator section 152 that serves as a discriminating unit.

The button discriminator section 152 discriminates whether the button, brought into contact with the contact site 151, corresponds to the gas supply and water supply button 35a with the resistor R1 or the carbon dioxide gas button 140 with the resistance R2. Further, when it is discriminated that the switch, brought into contact with the contact site 151, corresponds to the gas supply and water supply button 35a, the button discriminator section 152 outputs a signal, which is similar to, for instance, the gas supply and water supply signal to cause the gas supply for carbon dioxide gas to remain in the wait state, to, for instance, the announcement signal detector 57a of the ECR 51. In contrast, if the switch, brought into contact with the contact site 151, corresponds to the carbon dioxide gas button 140, the button discriminator section 152 outputs a signal, which is similar to the illumination signal mentioned above, to the announcement signal detector 57a of the ECR 51. With such operations, the luminal cavity gas supply control unit 57 outputs a command signal, resulting in the gas supply state to supply carbon dioxide gas to the luminal cavity.

While the present embodiment has been shown as having a structure in which the ECR 51 is connected to the second light source device 32, an alternative may take a structure wherein the gas supply apparatus 70 is connected to the second light source device 32.

Thus, with such a structure mentioned above, the gas supply and water supply button and the carbon dioxide gas button incorporates the electrical contacts with different resistances, respectively, and the manipulator of the endoscope is provided with the contact area with which the electrical contact is brought into contact. Also, the second light source device, to which the endoscope is connected, is provided with the button discriminator section for discriminating whether the button, disposed in the manipulator of the second light source device, corresponds to the gas supply and water supply button or the carbon dioxide gas button. Such an arrangement makes it possible to supply predetermined gas upon executing the operation to discriminate whether the button, disposed in the manipulator, corresponds to the gas supply and water supply button or the carbon dioxide button.

Moreover, an alternative may be configured such that instead of providing the resistors in the respective buttons 35a, 140 and providing the contact area 151 on the manipulator 35 while permitting the second light source device 32 to be provided with the button discriminator section 152, the operation is executed based on the measured values resulting from the flow rate sensor 56c, provided in the ECR 51, or the second flow rate sensor 79, provided in the gas supply apparatus 70, to render the ECR 51 or the gas supply apparatus 70 operative in a gas supply state to allow carbon dioxide gas to be supplied to a luminal cavity or inoperative in a gas supply interruptive state to interrupt the supply of gas to the luminal cavity.

Figure 27:
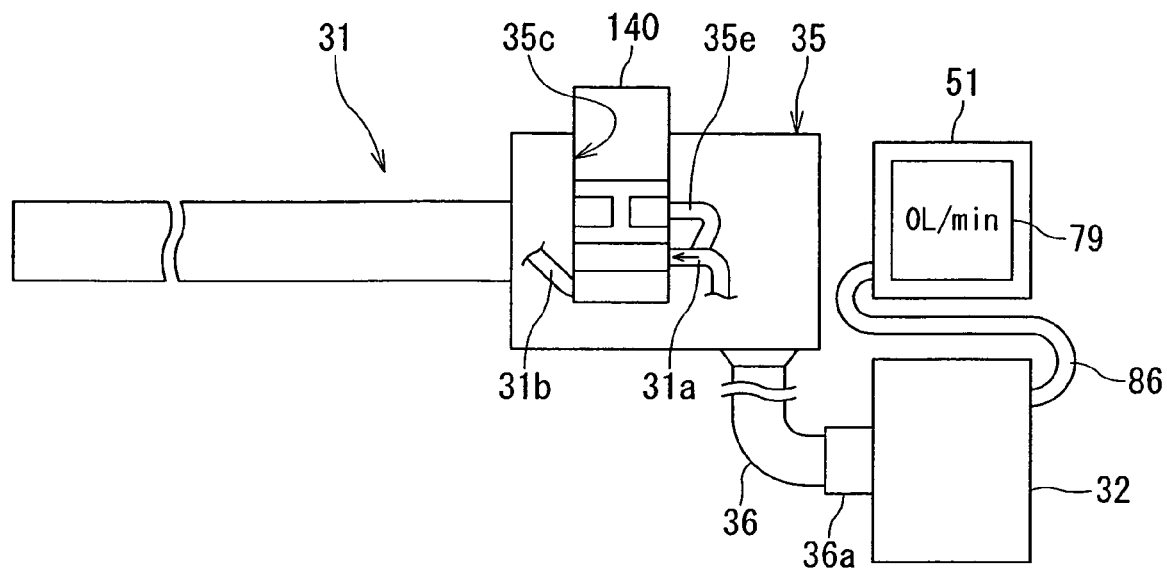
FIG. 27 is a view for illustrating the relationship between the carbon dioxide gas button, disposed in the gas supply and water supply cylinder, and the flow rate.
Figure 28:
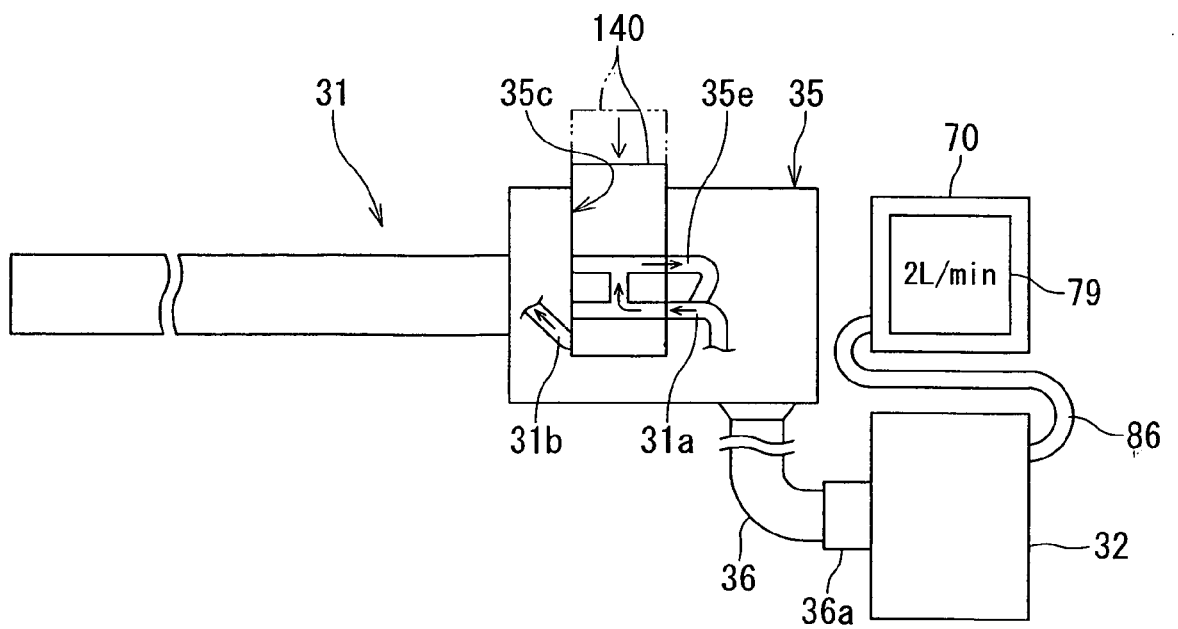
FIG. 28 is a view for illustrating the relationship between the carbon dioxide gas button, shifted to a gas supply position, and the flow rate.
Figure 29:
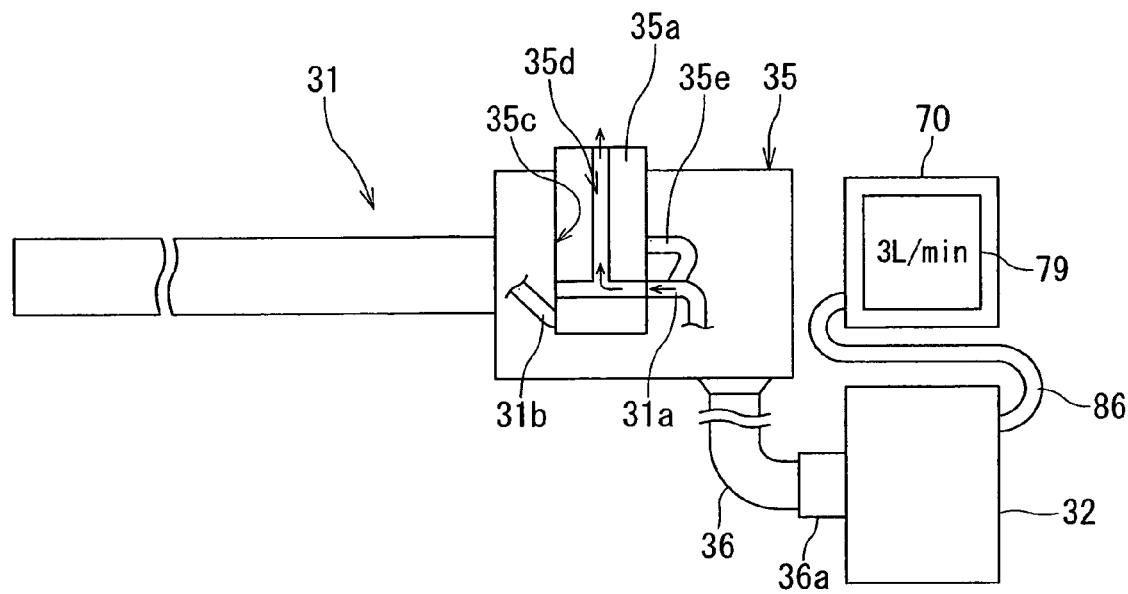
FIG. 29 is a view for illustrating the relationship between the carbon dioxide gas button, disposed in the gas supply and water supply cylinder, and the flow rate.

More particularly, as shown in FIGS. 27 to 29, such operation is executed upon utilizing the occurrence of a difference in the flow rate between a status wherein the button, placed in the gas supply and water supply cylinder 35c provided in the manipulator 35, is the gas supply and water supply button 35a and a status wherein the button, placed in the gas supply and water supply cylinder 35c, is the carbon dioxide gas button 140.

Under circumstances where the carbon dioxide gas button 140 is placed in the gas supply and water supply cylinder 35c as shown in FIG. 27 upon which the carbon dioxide gas button 140 remains in an inoperative state with no depressing operation, gas fed to the upstream gas supply conduit 31a can not flow beyond this place. For this reason, the measured value of the flow rate sensor 79 lies at a value of 0 L/min. On the contrary, when the carbon dioxide gas button 140 is pressed down in a manner as shown by an arrow in FIG. 28, gas flows from the upstream gas supply conduit 31a to the downstream gas supply conduit 31b in a manner as shown by an arrow. This results in variation in which the measured value of the flow rate sensor 79 lies at a value of, for instance, 2 L/min.

In the meanwhile, under circumstances where the gas supply and water supply button 35a is placed in the gas supply and water supply cylinder 35c, gas fed to the upstream gas supply conduit 31a leaks from the bore portion 35d. Therefore, the measured value of the flow rate sensor 79 lies at a value of, for instance, 3 L/min.

Figure 30:
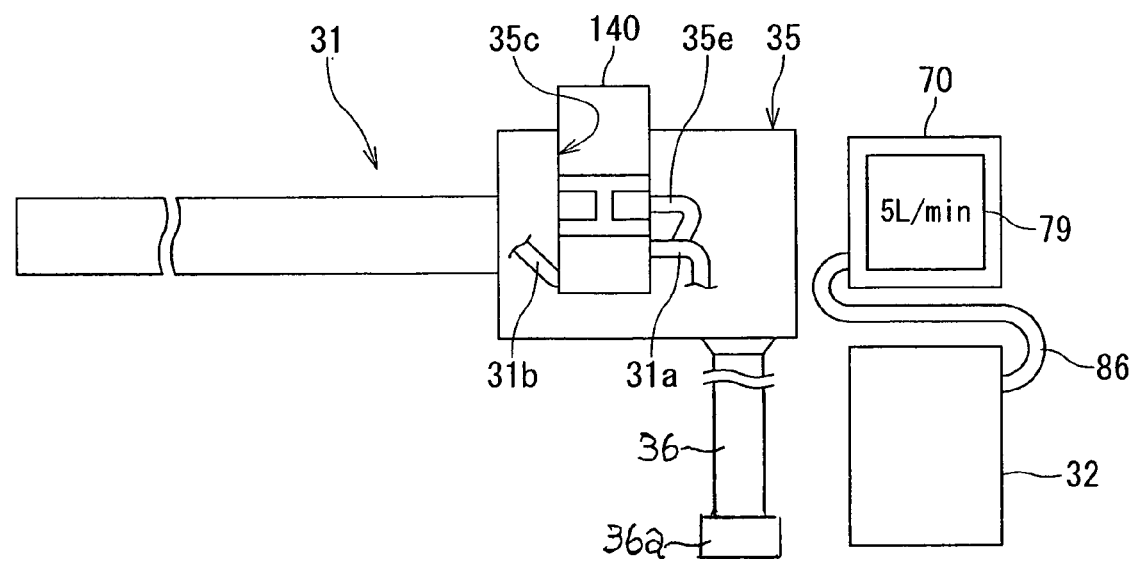
FIG. 30 is a view for illustrating the relationship between a status, wherein an endoscopic connector is removed from a light source device, and the flow rate

Moreover, under circumstances where the light source connector 36d is removed from the second light source device 32 as shown in FIG. 30, the measured value of the flow rate sensor 79 lies at a value of, for instance, 5 L/min regardless of the button located in the gas supply and water supply cylinder 35c under a condition where carbon dioxide gas is supplied to the luminal cavity from the gas supply apparatus 70.

Accordingly, with the presently filed embodiment, the measured value of the flow rate sensor 79 in the order of 2.5 L/min is set in the control unit 80 as a third threshold value and the measured value of the flow rate sensor 79 in the order of 5 L/min is set in the control unit 80 as a second threshold value.

With such setting, the control unit 80 executes the operation such that when discrimination is made that the measured value of the flow rate sensor 79 is less than the thirst threshold value, discrimination is made that the button, mounted in the gas supply and water supply cylinder 35 corresponds to the carbon dioxide gas button in intended use upon which the carbon dioxide gas supply state is continuously sustained. In contrast, if discrimination is made that the measured value of the flow rate sensor 79 is greater than the thirst threshold value, discrimination is made that the button, mounted in the gas supply and water supply cylinder 35 corresponds to the gas supply and water supply button 35a different from intended use upon which the operation is executed to switch the carbon dioxide gas supply state into the gas supply interruptive state.

Also, when the measured value of the flow rate sensor 79 indicates the second threshold value, for instance, the buzzer 56d is activated into the sound generating state to provide an alarm by which the operator is provided with notification of the occurrence of a defect in a mounted condition between the second light source device 32 and the light source connector 36d.

Further, while the present embodiment has been shown in the structure wherein the gas supply apparatus 70 is connected to the second light source device 32, an alternative may take a structure in which the ECR 51 is connected to the second light source device 32.

Thus, by making comparison between the measured value of the flow rate sensor and the threshold value, it becomes possible to discriminate whether the button, placed in the manipulator, corresponds to the switch in intended use. By so doing, when supplying carbon dioxide gas to the luminal cavity, placing the carbon dioxide gas in the manipulator enables wasteful consumption of carbon dioxide gas from the gas container to be more effectively suppressed.

No limitation is intended by the present invention to such various embodiments described above and the present invention may be possible to be implemented in a variety of modifications without departing from the spirit and scope of the present invention on stages for carrying out the embodiments. In addition, the various embodiments described above contain inventions in a variety of stages and various inventions may be reduced into practice upon suitable combinations between plural component parts that are disclosed.

What is claimed is:

1. An endoscopic system comprising:
an endoscope having an inserter section to be inserted into a body cavity of a specimen, an air and water supply device that supply air and water outside of the inserter section, an air delivery path through which air is supplied to a distal end of the inserter section, and a switch manually operated to allow the air to pass through the delivery path;
an illumination device for providing illumination to the distal end of the insertion section; and
an insufflation gas supply apparatus that supplies a predetermined type of insufflation gas to the body cavity via the air delivery path,
wherein the insufflation gas supply apparatus comprises:
a determination unit comprising circuitry for determining whether or not the insufflation gas supply apparatus needs to supply the insufflation gas to the body cavity, based on a signal received from the illumination device verifying whether the illumination device is in an operative state and a signal received from the air and water supply device verifying whether the air and water supply device is in an operative state; and
a control unit that automatically controls supply of the insufflation gas from the insufflation gas supply apparatus to the body cavity, depending on a determined result of the determination unit, wherein the control unit includes stop means that automatically stops the supply of the insufflation gas from the insufflation gas supply apparatus to the body cavity.

2. The endoscopic system according to claim 1, wherein:
the determination unit includes:
a detector detecting a signal indicative of the presence of or absence of a need to supply gas to the body cavity; and
a discriminator discriminating whether not the gas needs to be supplied to the body cavity depending on the signal detected by the detector.

3. The endoscopic system according to claim 2, wherein:
the signal detected by the detector includes a signal indicative of information as to whether or not the illumination for use in the endoscope is being irradiated.

4. The endoscopic system according to claim 3, wherein:
the endoscope includes a gas supply and water supply device through which gas and water are supplied to a distal end of the inserter section via an interior of the inserter section; and
wherein the signal, detected by the detector, includes a signal indicative of whether or not the illumination is irradiated from the illumination device,
and a signal indicative of whether of not the gas supply and water supply device provides gas supply and water supply.

5. The endoscopic system according to claim 3, wherein:
the endoscope includes a camera for picking up an observation site, and a camera control unit driving the camera and processing a signal picked up by the camera; and
wherein the signal, detected by the detector, includes a signal indicative of whether or not the illumination is irradiated from the illumination device, and a signal indicative of whether or not the camera control unit lies in an operative state.

6. The endoscopic system according to claim 2, further comprising:
an abdominal insufflation device supplying predetermined gas to an abdominal cavity of the specimen; and
wherein the signal includes a signal indicative of a status in which the abdominal insufflation device supplies the gas to the abdominal cavity.

7. The endoscopic system according to claim 2, further comprising:
a light source device supplying configured to supply at least an illumination light onto the endoscope; and
wherein the endoscope is detachably connected to the light source device via a connector; and
the signal, detected by the detector, includes a signal indicative of whether or not the connector of the endoscope is connected to the light source device.

8. The endoscopic system according to claim 1, wherein:
the determination unit includes means for calculating a total volume of gas supplied from the gas supply apparatus, and means for determining whether or not the gas needs to be supplied to the body cavity.

9. The endoscopic system according to claim 1, wherein:
the insufflation gas is a carbon dioxide gas;
the determination unit includes:
calculation means that calculates a duration of the supply of the carbon dioxide gas to be supplied from the insufflation gas supply apparatus, and
a timer that measures an actual duration of the supply of the carbon dioxide gas; and
stop means that stops the supply of the carbon dioxide gas when the actual duration reaches the duration calculated by the calculation means.

10. The endoscopic system according to claim 1, wherein:
the insufflation gas is a carbon dioxide gas;
the determination unit includes;
calculation means that calculates a duration in which no variation takes place in a pressure of the carbon dioxide gas supplied from the insufflation gas supply apparatus, and
determination means that determines whether or not the carbon dioxide gas needs to be supplied to the body cavity depending on whether or not the calculated duration reaches a predetermined value; and
stop means that stops the supply of the carbon dioxide gas when the calculated duration reaches the predetermined value.

* * * * *